United States Patent
Morgan et al.

(10) Patent No.: US 9,266,960 B2
(45) Date of Patent: Feb. 23, 2016

(54) ANTI-EPIDERMAL GROWTH FACTOR RECEPTOR VARIANT III CHIMERIC ANTIGEN RECEPTORS AND USE OF SAME FOR THE TREATMENT OF CANCER

(75) Inventors: Richard A. Morgan, Columbia, MD (US); Steven A. Rosenberg, Potomac, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/110,189

(22) PCT Filed: Mar. 21, 2012

(86) PCT No.: PCT/US2012/029861
§ 371 (c)(1),
(2), (4) Date: Oct. 24, 2013

(87) PCT Pub. No.: WO2012/138475
PCT Pub. Date: Oct. 11, 2012

(65) Prior Publication Data
US 2014/0037628 A1 Feb. 6, 2014

Related U.S. Application Data

(60) Provisional application No. 61/473,409, filed on Apr. 8, 2011.

(51) Int. Cl.
| | |
|---|---|
| *C07K 16/32* | (2006.01) |
| *C07K 14/705* | (2006.01) |
| *C07K 14/725* | (2006.01) |
| *C07K 16/28* | (2006.01) |
| *C07K 16/30* | (2006.01) |
| *A61K 39/00* | (2006.01) |
| *A61K 38/00* | (2006.01) |

(52) U.S. Cl.
CPC ............ *C07K 16/32* (2013.01); *C07K 14/7051* (2013.01); *C07K 14/70503* (2013.01); *C07K 14/70517* (2013.01); *C07K 14/70521* (2013.01); *C07K 14/70575* (2013.01); *C07K 14/70596* (2013.01); *C07K 16/2863* (2013.01); *C07K 16/3053* (2013.01); *A61K 38/00* (2013.01); *A61K 2039/505* (2013.01); *C07K 2317/21* (2013.01); *C07K 2319/00* (2013.01); *C07K 2319/70* (2013.01)

(58) Field of Classification Search
None
See application file for complete search history.

(56) References Cited

U.S. PATENT DOCUMENTS

| | | | |
|---|---|---|---|
| 3,832,253 A | 8/1974 | Di Palma et al. |
| 3,854,480 A | 12/1974 | Zaffaroni |
| 4,235,871 A | 11/1980 | Papahadjopoulos et al. |
| 4,450,150 A | 5/1984 | Sidman |
| 4,452,775 A | 6/1984 | Kent |
| 4,501,728 A | 2/1985 | Geho et al. |
| 4,667,014 A | 5/1987 | Nestor, Jr. et al. |
| 4,748,034 A | 5/1988 | De Rham |
| 4,837,028 A | 6/1989 | Allen |
| 5,019,369 A | 5/1991 | Presant et al. |
| 5,075,109 A | 12/1991 | Tice et al. |
| 5,087,616 A | 2/1992 | Myers et al. |
| 5,225,539 A | 7/1993 | Winter |
| 5,239,660 A | 8/1993 | Ooi |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobivits |
| 6,265,150 B1 | 7/2001 | Terstappen et al. |
| 7,628,986 B2 | 12/2009 | Weber et al. |
| 2002/0197266 A1 | 12/2002 | Debinski |
| 2005/0053608 A1 | 3/2005 | Weber et al. |
| 2006/0269529 A1 | 11/2006 | Niederman et al. |
| 2010/0105136 A1 | 4/2010 | Carter et al. |

FOREIGN PATENT DOCUMENTS

| | | |
|---|---|---|
| EP | 0 239 400 B1 | 8/1994 |
| GB | 2 188 638 A | 10/1987 |
| WO | WO 2005/010151 A2 | 2/2005 |
| WO | WO 2008/045437 A2 | 4/2008 |
| WO | WO 2010/025177 A1 | 3/2010 |
| WO | WO 2011/041093 A1 | 4/2011 |

OTHER PUBLICATIONS

Bullain et al., "Genetically engineered T cells to target EGFRvIII expressing glioblastoma," *Journal of Neuro-Oncology*, 94, 373-382 (2009).
Capecchi et al., "High efficiency transformation by direct microinjection of DNA incto cultured mammalian cells," *Cell*, 22, 479-488 (1980).
CBTRUS 2008 Statistical Report: Primary brain tumors in the United States; CBTRUS (2008).
Chu et al., "SV40 DNA transfection of cells in suspension: analysis of the efficiency of transcription and translation of T-antigen," *Gene*, 13, 197-202 (1981).
Clay et al., "Efficient transfer of a tumor antigen-reactive TCR to human peripheral blood lymphocytes confers anti-tumor reactivity," *J. Immunol.*, 163, 507-513 (1999).
Felgner et al., "Lipofection: a highly efficient, lipid-mediated DNA-transfection procedure," *Proc. Natl. Acad. Sci. USA*, 84, 7413-7417 (1987).

(Continued)

*Primary Examiner* — Ruixiang Li
(74) *Attorney, Agent, or Firm* — Leydig, Voit & Mayer

(57) ABSTRACT

The disclosure provides chimeric antigen receptors (CARs) comprising an antigen binding domain of human antibody 139, an extracellular hinge domain, a transmembrane domain, and an intracellular domain T cell receptor signaling domain. Nucleic acids, recombinant expression vectors, host cells, populations of cells, antibodies, or antigen binding portions thereof, and pharmaceutical compositions relating to the CARs are disclosed. Methods of detecting the presence of cancer in a host and methods of treating or preventing cancer in a host are also disclosed.

2 Claims, 7 Drawing Sheets

(56) References Cited

OTHER PUBLICATIONS

Figure 3B:
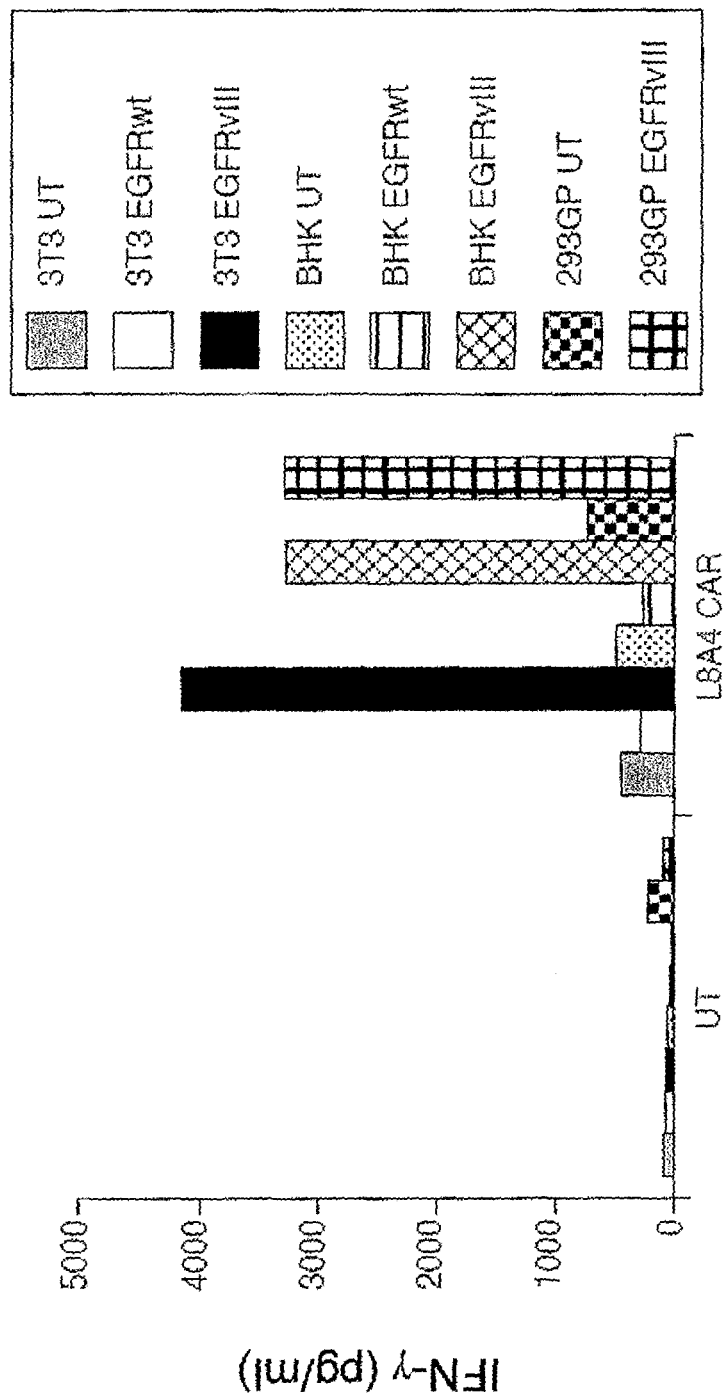

Ge et al., "Immunotherapy of brain cancers: the past, the present, and future directions," *Clinical and Developmental Immunology*, 2010, 1-19 (Mar. 2011).
Graham et al., "A new technique for the assay of infectivity of human adenovirus 5 DNA," *Virology*, 52, 456-467 (1973).
Haskard et al., "The production of human monoclonal autoantibodies from patients with rheumatoid arthritis by the EBV-hybridoma technique," *J. Immunol. Methods*, 74 (2), 361-367 (1984).
Hudecz, "Synthesis of peptide bioconjugates," *Methods Mol. Biol.*, 298, 209-223 (2005).
Huse et al., "Generation of a large combinatorial library of the immunoglobulin repertoire in phage lambda," *Science*, 246 (4935), 1275-1281 (1989).
International Search Report, International Application No. PCT/US2012/029861 dated May 21, 2012.
Jemal et al., "Cancer statistics, 2007" *Cancer J. Clin.*, 57, 43-66 (2007).
Keeling et al., "Vacuolar H+-ATPases: targets for drug discovery?" *Annals New York Academy of Sciences*, 834, 600-608 (1997).
Klein et al., "High-velocity microprojectiles for delivering nucleic acids into living cells," *Nature*, 327, 70-73 (1987).
Kirin et al., "Amino acid and peptide bioconjugates of copper(II) and zinc(II) complexes with a modified N,N-bis(2-picolyl)amine ligand," *Inorg Chem.*, 44 (15), 5405-5415 (2005).
Köhler et al., "Derivation of specific antibody-producing tissue culture and tumor lines by cell fusion," *Eur. J. Immunol.*, 6 (7), 511-519 (1976).
Mannino et al., "Liposome mediated gene transfer," BioTechniques, 6, 682-690 (1988).
Marquardt et al., "Involvement of vacuolar H$^+$adenosine triphosphatase activity in multidrug resistance in HL60 cells," *J. Natl. Cancer Inst.*, 83 (15), 1098-1102 (1991).
Mellman et al., "Acidification of the endocytic and exocytic pathways," *Ann. Rev. Biochem.*, 55, 663-700 (1986).
Morgan et al., "Recognition of glioma stem cells by genetically modified t Cells targeting EGFRvIII and development of adoptive cell therapy for glioma," *Human Gene Therapy*, 23, 1043-1053 (Sep. 24, 2012).
Nelson, "Structure and Pharmacology of the Proton-ATPases," *Trends in Pharmacology Sciences*, 12, 71-75 (Feb. 1991).
Ohno et al., "Retrovirally engineered T-cell-based immunotherapy targeting type III variant epidermal growth factor receptor, a glioma-associated antigen," *Cancer Science*, 101(12), 2518-24 (Dec. 2010).
Pedersen et al., "Comparison of surface accessible residues in human and murine immunoglobulin Fv domains. Implication for humanization of murine antibodies," *J. Mol. Biol.*, 235 (3), 959-973 (1994).
Reiter et al., "Engineering interchain disulfide bonds into conserved framework regions of Fv fragments: improved biochemical characteristics of recombinant immunotoxins containing disulfide-stabilized Fv," *Protein Eng.*, 7 (5), 697-704 (1994).
Riddell et al., "The use of anti-CD3 and anti-CD28 monoclonal antibodies to clone and expand human antigen-specific T cells," *J. Immunol. Methods*, 128, 189-201 (1990).
Roder et al., "The EBV-hybridoma technique," *Methods Enzymol.*, 121, 140-167 (1986).
Sadelain et al., "The promise and potential pitfalls of chimeric antigen receptors," *Current Opinion in Immunology*, 21, 215-223 (2009).
Shigekawa et al., "Electroporation of eukaryotes and prokaryotes: a general approach to the introduction of macromolecules into cells," *BioTechniques*, 6, 742-751 (1988).
Sonabend et al., "Targeting epidermal growth factor receptor variant III: a novel strategy for the therapy of malignant glioma," *Expert Rev. Anticancer Ther.*, 7, 545-550 (2007).
Szoka, "Comparative properties and methods of preparation of lipid vesicles (liposomes)," *Ann. Rev. Biophys. Bioeng.*, 9, 467-508 (1980).
Wadwa et al., "Receptor mediated glycotargeting," *J. Drug Target.*, 3 (2), 111-127 (1995).
Wassarman, "The biology and chemistry of fertilization," *Science*, 235, 553-560 (1987).
Written Opinion in PCT/US2012/029861 dated May 21, 2012.
Zhao et al., "Primary human lymphocytes transduced with NY-ESO-1 antigen-specific TCR genes recognize and kill diverse human tumor cell lines," *J. Immunol.*, 174, 4415-4423 (2005).
Natsume et al., "Genetically-Engineered T-Cell Based Immunotherapy Targeting EGFRvIII," *Biotherapy*, 24 (6), 474-481 (2010).

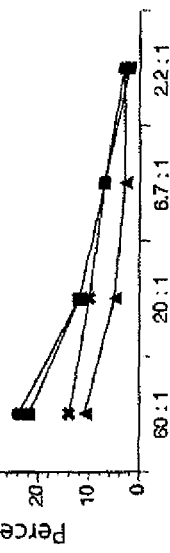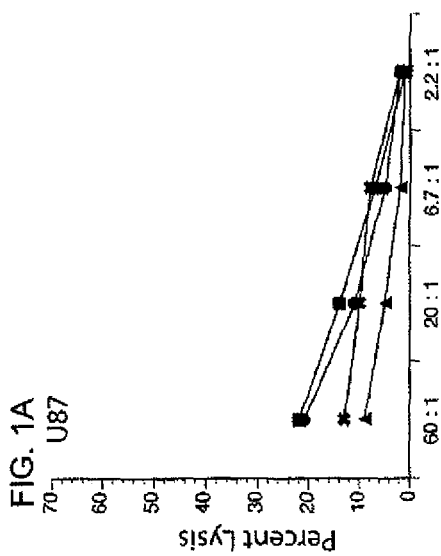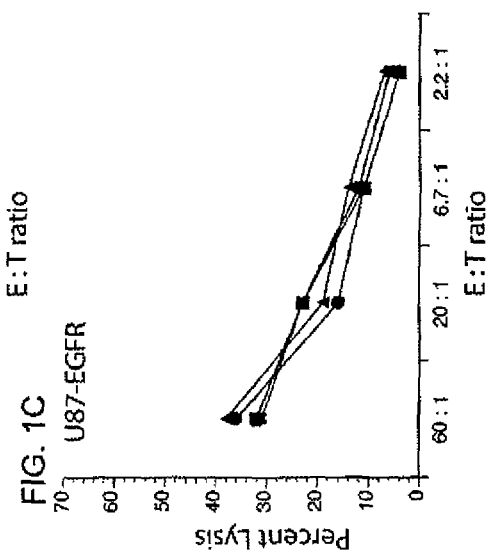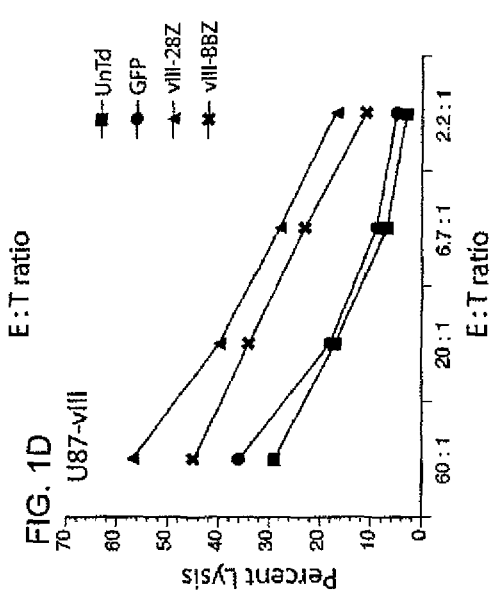

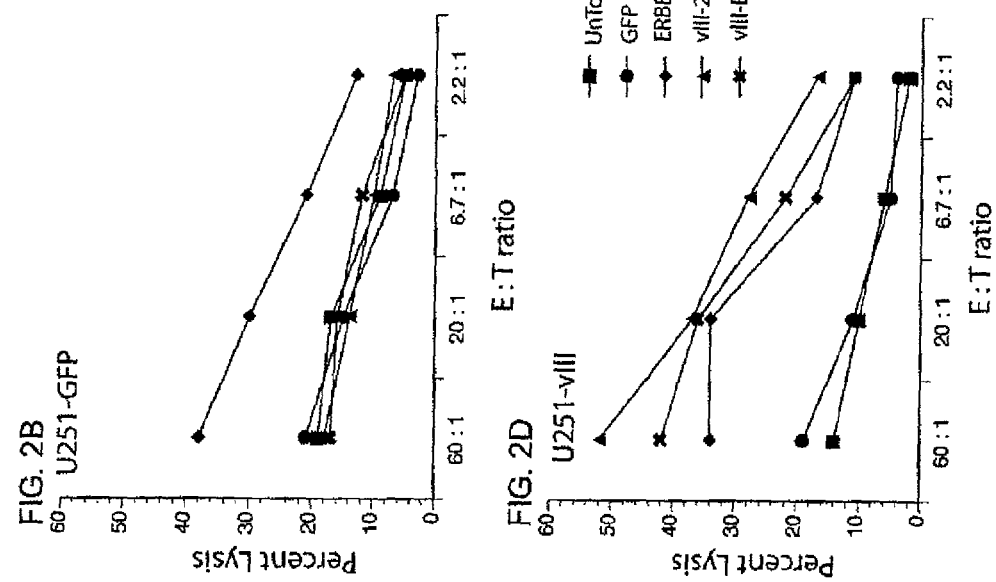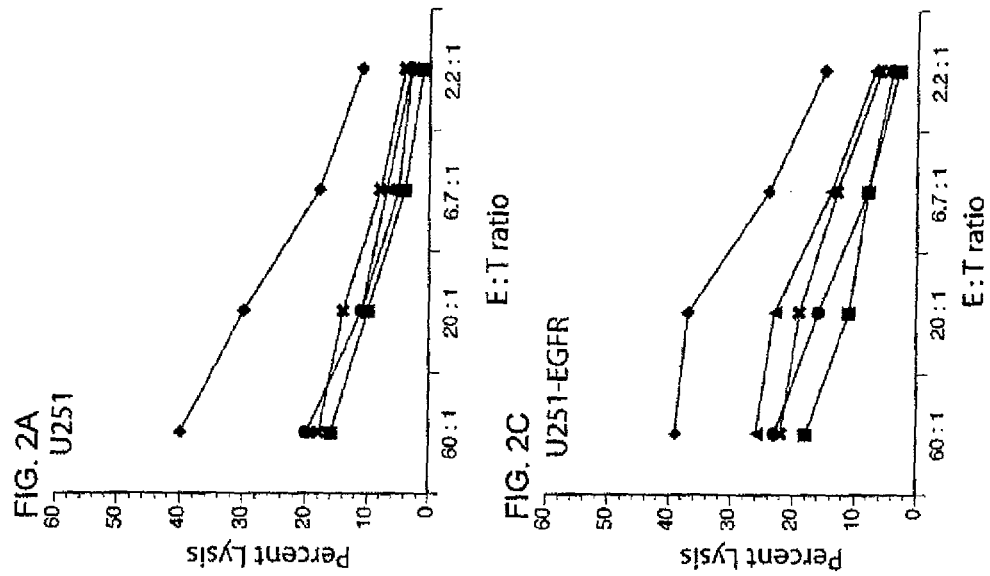

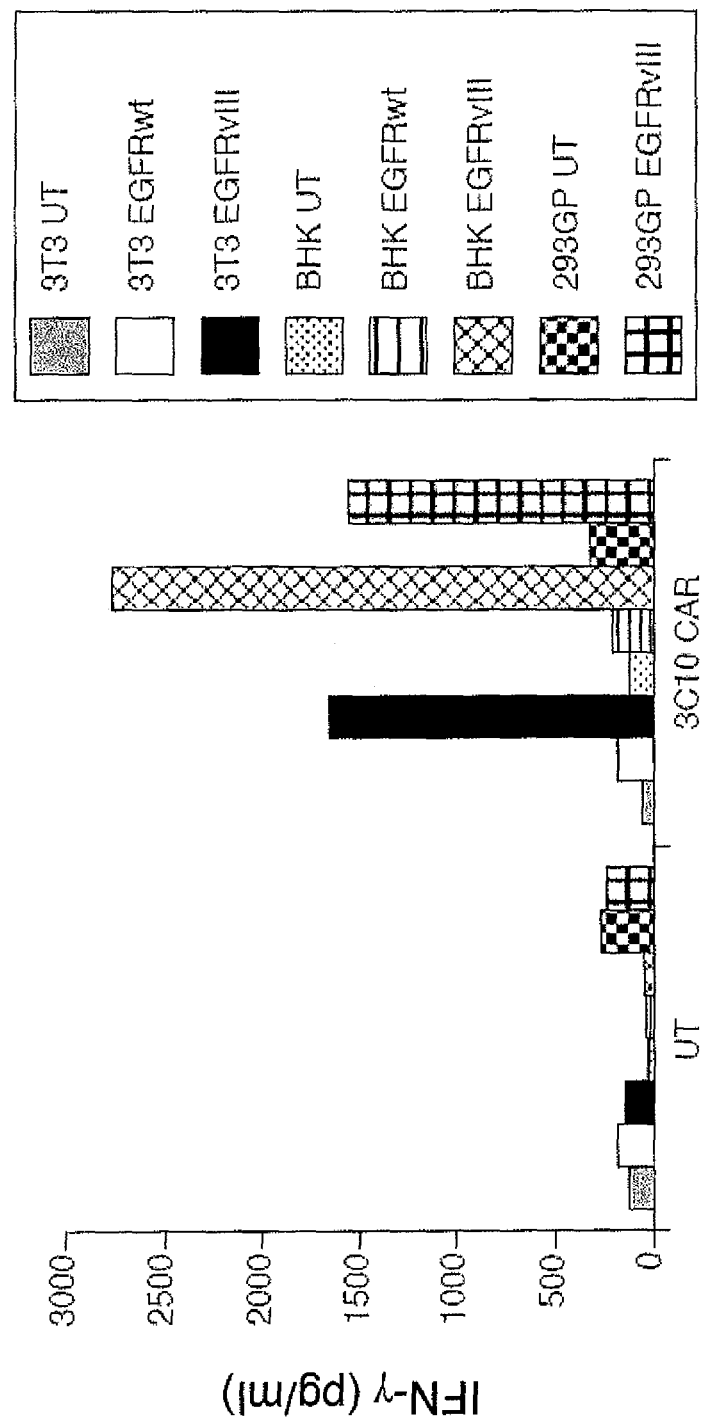

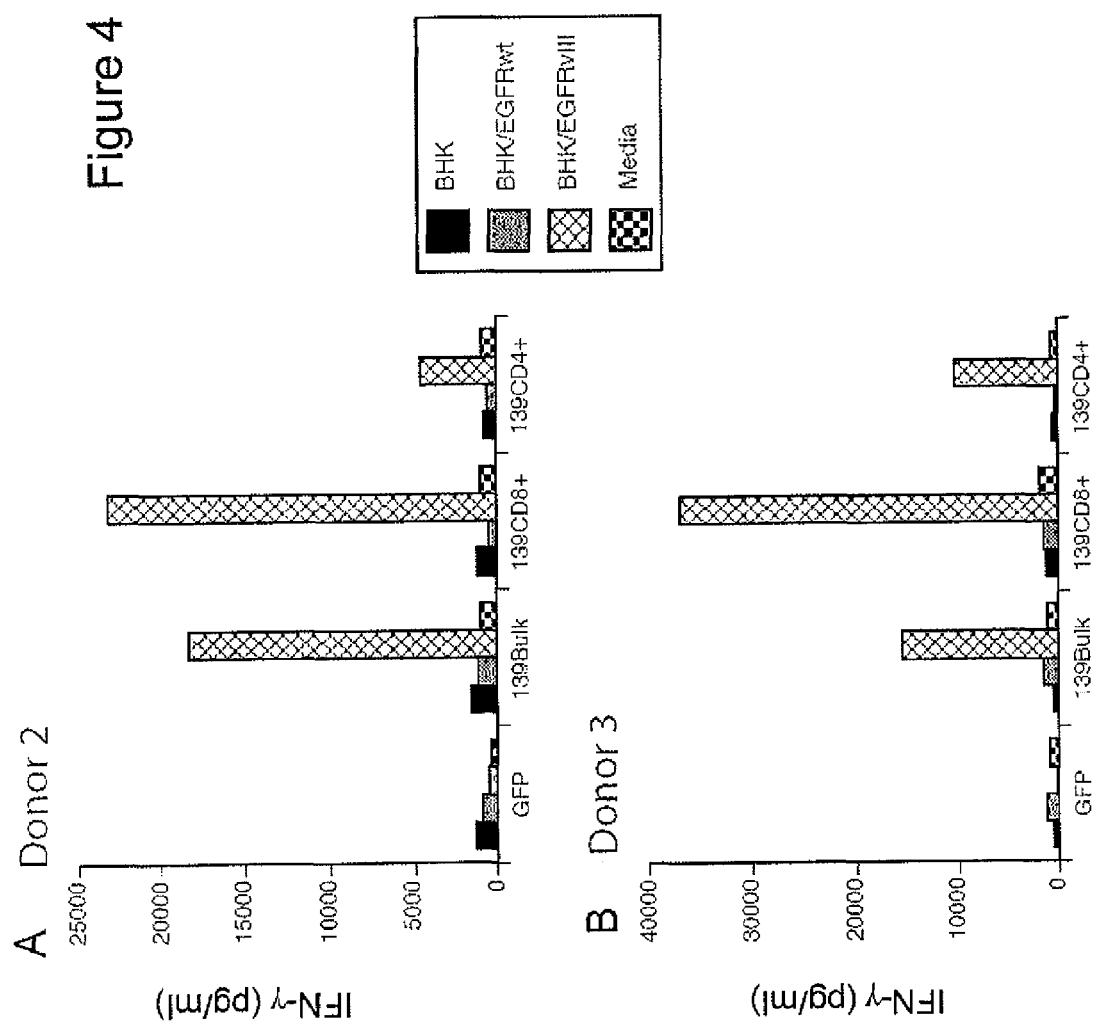

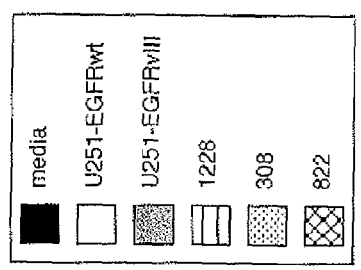
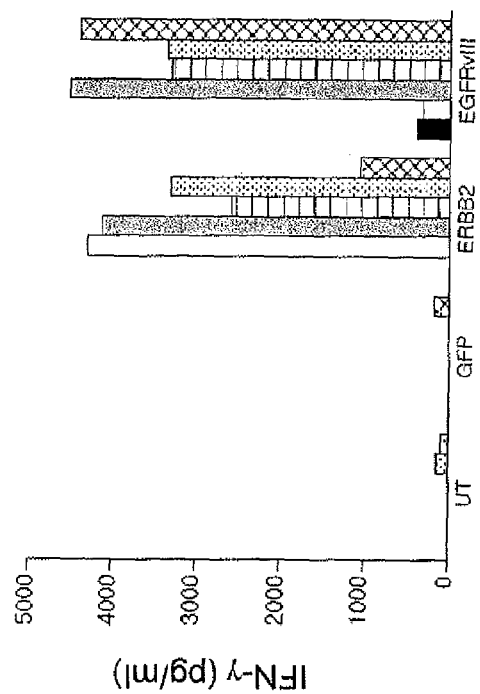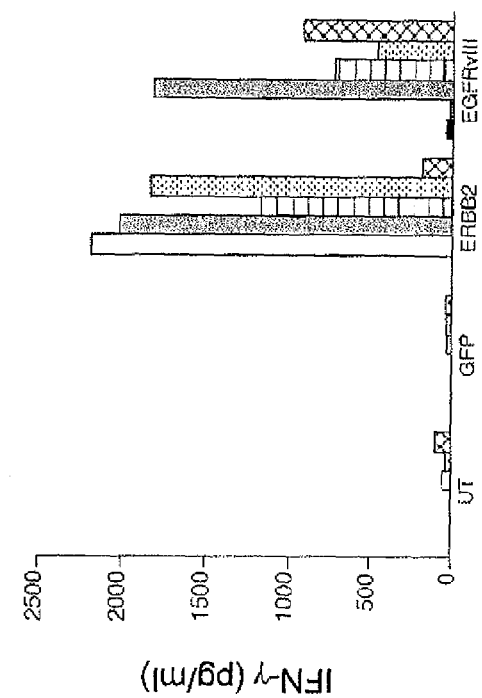
Figure 5

ANTI-EPIDERMAL GROWTH FACTOR RECEPTOR VARIANT III CHIMERIC ANTIGEN RECEPTORS AND USE OF SAME FOR THE TREATMENT OF CANCER

CROSS-REFERENCE TO RELATED APPLICATION

This patent application is the U.S. national phase of International Patent Application No. PCT/US2012/029861, filed Mar. 21, 2012, which claims the benefit of U.S. Provisional Patent Application Ser. No. 61/473,409, filed Apr. 8, 2011, each of which is incorporated by reference in its entirety herein.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 27,793 Byte ASCII (Text) file named "714239-2 ST25.txt," dated Apr. 30, 2015.

BACKGROUND OF THE INVENTION

The American Cancer Society estimates that approximately 20,500 new cases of primary brain and nervous system tumors will develop and approximately 12,740 patients will die in the U.S. each year (Jemal et al., *Cancer J. Clin.*, 57:43-66 (2007)) as a result of these cancers. Brain tumors account for approximately 85 to 90% of all central nervous system malignancies. Glioblastoma is the most aggressive and most common glioma accounting for 51% of all gliomas (CB-TRUS 2008 Statistical Report: Primary Brain Tumors in the United States—CBTRUS, 2000-2004 (2008)). Despite advances in conventional treatments such as surgical resection, radiation therapy, and chemotherapy, the prognosis for gliomas, as well as other types of brain and nervous system cancer, may be poor. For example, most patients with glioblastoma multiforme (GBM) survive less than 15 months from diagnosis. Accordingly, there exists an unmet need for additional treatments for cancer, particularly gliomas.

BRIEF SUMMARY OF THE INVENTION

An embodiment of the invention provides chimeric antigen receptors (CARs) comprising an antigen binding domain of human antibody 139, an extracellular hinge domain, a transmembrane domain, and an intracellular T cell signaling domain.

Further embodiments of the invention provide related nucleic acids, recombinant expression vectors, host cells, populations of cells, antibodies, or antigen binding portions thereof, and pharmaceutical compositions relating to the CARs of the invention.

Additional embodiments of the invention provide methods of detecting the presence of cancer in a host and methods of treating or preventing cancer in a host.

BRIEF DESCRIPTION OF THE SEVERAL VIEWS OF THE DRAWING(S)

FIG. 1A is a graph showing the specific lysis (percent lysis) of $^{51}$Cr labeled parent U87 glioblastoma tumor cell line ("U87") (target cell) by human peripheral blood lymphocytes (PBL) (effector cells) that were untransduced (UnTd) (■) or transduced with vectors encoding green fluorescent protein (GFP) (●), SEQ ID NO: 10 (h139Ab-hCD828BBZ CAR) (x), or SEQ ID NO: 11 (h139Ab-hCD28Z) (▲) at various effector to target ratios (E:T ratio).

FIG. 1B is a graph showing the specific lysis (percent lysis) of $^{51}$Cr labeled U87-GFP (expressing GFP) glioblastoma tumor cell line (target cell) by human PBL (effector cells) that were untransduced (UnTd) (■) or transduced with vectors encoding GFP (●), SEQ ID NO: 10 (h139Ab-hCD828BBZ CAR) (x), or SEQ ID NO: 11 (h139Ab-hCD28Z) (▲) at various effector to target ratios (E:T ratio).

FIG. 1C is a graph showing the specific lysis (percent lysis) of $^{51}$Cr labeled U87-EGFR glioblastoma tumor cell line (expressing wild-type epidermal growth factor receptor) (target cell) by human PBL (effector cells) that were untransduced (UnTd) (■) or transduced with vectors encoding GFP (●), SEQ ID NO: 10 (h139Ab-hCD828BBZ CAR) (x), or SEQ ID NO: 11 (h139Ab-hCD28Z) (▲) at various effector to target ratios (E:T ratio).

FIG. 1D is a graph showing the specific lysis (percent lysis) of $^{51}$Cr labeled U87-vIII glioblastoma tumor cell line (expressing EGFRvIII) (target cell) by human PBL (effector cells) that were untransduced (UnTd) (■) or transduced with vectors encoding GFP (●), SEQ ID NO: 10 (h139Ab-hCD828BBZ CAR) (x), or SEQ ID NO: 11 (h139Ab-hCD28Z) (▲) at various effector to target ratios (E:T ratio).

FIG. 2A is a graph showing the specific lysis (percent lysis) of $^{51}$Cr labeled parent U251 glioblastoma tumor cell line (target cell) by human PBL (effector cells) that were untransduced (UnTd) (■) or transduced with vectors encoding green fluorescent protein (GFP) (●), anti-ERBB2 CAR (♦), SEQ ID NO: 10 (h139Ab-hCD828BBZ CAR) (x), or SEQ ID NO: 11 (h139Ab-hCD28Z) (▲) at various effector to target ratios (E:T ratio).

FIG. 2B is a graph showing the specific lysis (percent lysis) of $^{51}$Cr labeled U25'-GFP glioblastoma tumor cell line (expressing GFP) (target cell) by human PBL (effector cells) that were untransduced (UnTd) (■) or transduced with vectors encoding green fluorescent protein (GFP) (●), anti-ERBB2 CAR (♦), SEQ ID NO: 10 (h139Ab-hCD828BBZ CAR) (x), or SEQ ID NO: 11 (h139Ab-hCD28Z) (▲) at various effector to target ratios (E:T ratio).

FIG. 2C is a graph showing the specific lysis (percent lysis) of $^{51}$Cr labeled U251-EGFR glioblastoma tumor cell line (expressing wild-type EGFR) (target cell) by human PBL (effector cells) that were untransduced (UnTd) (■) or transduced with vectors encoding green fluorescent protein (GFP) (●), anti-ERBB2 CAR (♦), SEQ ID NO: 10 (h139Ab-hCD828BBZ CAR) (x), or SEQ ID NO: 11 (h139Ab-hCD28Z) (▲) at various effector to target ratios (E:T ratio).

FIG. 2D is a graph showing the specific lysis (percent lysis) of $^{51}$Cr labeled U251-vIII glioblastoma tumor cell line (expressing wild-type EGFRvIII) (target cell) by human PBL (effector cells) that were untransduced (UnTd) (■) or transduced with vectors encoding green fluorescent protein (GFP) (●), anti-ERBB2 CAR (♦), SEQ ID NO: 10 (h139Ab-hCD828BBZ CAR) (x), or SEQ ID NO: 11 (h139Ab-hCD28Z) (▲) at various effector to target ratios (E:T ratio).

Figure 3C:
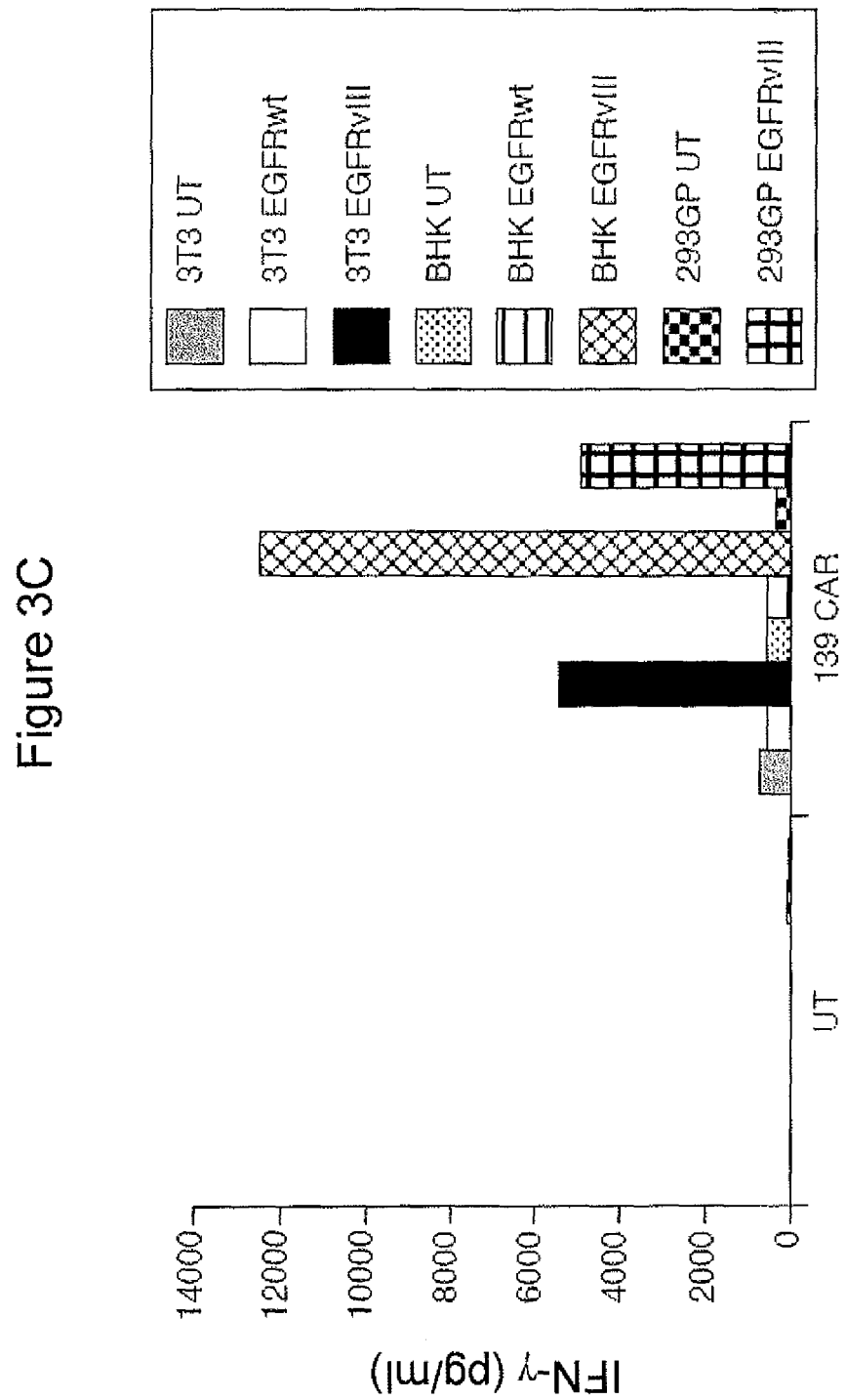

FIGS. 3A-3C are graphs showing interferon (IFN)-γ secretion as measured by ELISA (pg/ml, mean of triplicate determinations) by untransduced cells (UT) or human T cells transduced with 3C10 CAR (FIG. 3A), L8A4 CAR (FIG. 3B), h139Ab-hCD28Z CAR (FIG. 3C) upon co-culture with target cells lines untransduced NIH-3T3 (3T3) (3T3 UT grey bars), untransduced BHK (BHK UT, dotted bars), untransduced 293GP (293GP UT, checkered bars), EGFR-wild type transduced 3T3 (3T3 EGFRwt, white bars), EGFR-wild type transduced BHK (BHK EGFRwt, striped bars), EGFRvIII-transduced 3T3 (3T3 EGFRvIII, black bars), EGFRvIII-transduced BHK (BHK EGFRvIII, cross-hatched bars), or EGFRvIII-transduced 293GP (293GP EGFRvIII, bars with vertical and horizontal stripes).

FIGS. 4A and 4B are graphs showing IFN-γ secretion as measured by ELISA (pg/ml, mean of triplicate determinations) by T-cells from Donor 2 (FIG. 4A) or Donor 3 (FIG. 4B) that were transduced with green-fluorescent protein (GFP) or the 139-28Z vector (unsorted) (139bulk), or T cells that were transduced with the h139Ab-hCD28Z vector and then bead sorted into CD8 and CD4 enriched (>96%+) T cell populations (139CD8+ and 139CD4+). IFN-γ was measured upon co-culture of the transduced cells overnight with BHK target cells (black bars), EGFR wild type engineered BHK cells (EGFRwt, grey bars) or EGFRvIII engineered BHK cells (EGFRvIII, cross-hatched bars) or media (checkered bars).

FIGS. 5A and 5B are graphs showing IFN-γ secretion by T cells from human Donor 4 (FIG. 5A) and human Donor 5 (FIG. 5B) that were untransduced (UT) or transduced with anti-EGFRvIII CAR vector (139-28BBZ) (EGFRvIII), a GFP expressing vector (GFP), or a CAR vector targeting ERBB2. Transduced T cells were co-cultured with media (black bars), wild type EGFR engineered U251 cells (U251-EGFRwt, white bars), EGFR variant III engineered U251 cells (U251-EGFRvIII, grey bars), or glioma stem cell lines 1228 (bars with horizontal), 308 (dotted bars), or 822 (cross-hatched bars).

DETAILED DESCRIPTION OF THE INVENTION

An embodiment of the invention provides chimeric antigen receptors (CARs) comprising an antigen binding domain of human antibody 139 (h139Ab), an extracellular hinge domain, a transmembrane domain, and an intracellular T cell signaling domain.

A chimeric antigen receptor (CAR) is an artificially constructed hybrid protein or polypeptide containing the antigen binding domains of an antibody (e.g., scFv) linked to T-cell signaling domains. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

The phrases "have antigen specificity" and "elicit antigen-specific response" as used herein means that the CAR can specifically bind to and immunologically recognize an antigen, such that binding of the CAR to the antigen elicits an immune response.

The CARs of the invention have antigen specificity for epidermal growth factor receptor variant III (EGFRvIII). EGFRvIII is a variant of the epidermal growth factor receptor (EGFR), which is a transmembrane glycoprotein that is a member of the protein kinase superfamily. EGFRvIII is the most prevalent of several EGFR mutations found in human gliomas, and is expressed in about 30% to about 50% of glioblastoma multiforme (GBM) (also known as "glioblastoma"). The expression of EGFRvIII results from intragene deletion rearrangements that eliminate EGFR exons 2-7, and cause the joining of exons 1 and 8 of the coding sequences. EGFRvIII is expressed by tumor cells of various cancers such as, e.g., glioblastoma (including glioblastoma stem cells); breast, ovarian, and non-small cell lung carcinomas; head and neck squamous cell carcinoma; medulloblastoma, colorectal cancer, prostate cancer, and bladder carcinoma. Without being bound to a particular theory or mechanism, it is believed that by eliciting an antigen-specific response against EGFRvIII, the inventive CARs provide for one or more of the following: targeting and destroying EGFRvIII-expressing tumor cells, reducing or eliminating tumors, facilitatating infiltration of immune cells to the tumor site, and enhancing/extending anti-tumor responses. Because EGFRvIII is not expressed in normal (i.e., non-cancerous) tissue, it is contemplated that the inventive CARs advantageously substantially avoid targeting/destroying normal tissues and cells.

The invention provides a CAR comprising an antigen binding domain of human antibody 139. Antibody 139 is a human, anti-EGFRvIII antibody. Antibody 139 specifically binds to EGFRvIII. Suitable human antibody 139 sequences are disclosed in, for example, U.S. Pat. No. 7,628,986, which is hereby incorporated by reference. In this regard, a preferred embodiment of the invention provides CARs comprising an antigen-binding domain comprising, consisting of, or consisting essentially of, a single chain variable fragment (scFv) of human antibody 139.

Human antibody 139 comprises a light chain variable region and a heavy chain variable region. The light chain variable region may comprise, consist of, or consist essentially of SEQ ID NO: 1. The heavy chain variable region may comprise, consist, or consist essentially of SEQ ID NO: 2. Accordingly, in an embodiment of the invention, the antigen binding domain comprises a light chain variable region comprising SEQ ID NO: 1 and/or a heavy chain variable region comprising SEQ ID NO: 2.

In an embodiment, the antigen binding domain comprises a linker peptide. The linker peptide may be positioned between the light chain variable region and the heavy chain variable region. In this regard, the antigen binding domain may comprise a linker peptide comprising, consisting of, or consisting essentially of SEQ ID NO: 3.

In an embodiment, the antigen binding domain comprises a leader sequence. The leader sequence may be positioned at the amino terminus of the light chain variable region. In this regard, the antigen binding domain may comprise a leader sequence comprising, consisting of, or consisting essentially of SEQ ID NO: 4.

In an embodiment, the antigen binding domain may comprise a leader sequence, a light chain variable region, a linker peptide, and a heavy chain variable region. In this regard, the antigen binding domain comprising a leader sequence, a light chain variable region, a linker peptide, and a heavy chain variable region comprises, consists of, or consists essentially of SEQ ID NO: 5 (scFv human antibody 139).

In an embodiment of the invention, the CAR comprises an extracellular hinge domain, a transmembrane domain, and optionally, an intracellular hinge domain comprising CD8 and an intracellular T cell signaling domain comprising CD28, 4-1BB, and CD3ζ. CD28 is a T cell marker important in T cell co-stimulation. CD8 is also a T cell marker. 4-1BB transmits a potent costimulatory signal to T cells, promoting differentiation and enhancing long-term survival of T lymphocytes. CD3ζ associates with TCRs to produce a signal and contains immunoreceptor tyrosine-based activation motifs (ITAMs). In this regard, a preferred embodiment of the invention provides an extracellular hinge domain and transmembrane domain comprising, consisting essentially of, or consisting of, SEQ ID NO: 6 (human CD8 extracellular hinge domain and transmembrane domain). The intracellular T cell signaling domain comprises, consists essentially of, or consists of, SEQ ID NO: 7 (human CD28, 4-1BB, and CD3ζ intracellular T cell signaling domains).

In another embodiment of the invention, the CAR comprises an extracellular hinge domain, transmembrane domain, and intracellular T cell signaling domain comprising CD28 and CD3ζ. In this regard, a preferred embodiment of the invention provides an extracellular hinge domain, transmembrane domain, and intracellular T cell signaling domain comprising, consisting essentially of, or consisting of, SEQ ID NO: 8 (human CD28 extracellular hinge, transmembrane domain, and intracellular T cell signaling domains) and SEQ ID NO: 9 (human CD3ζ intracellular T cell signaling domain).

Additional embodiments of the invention provide CARs comprising, consisting of, or consisting essentially of any of the amino acid sequences set forth in Table 1.

TABLE 1

| Sequence | scFv | Further Components |
|---|---|---|
| SEQ ID NO: 10 (h139Ab-hCD828BBZ) | human antibody 139 | Human CD8 extracellular hinge and transmembrane domains<br>Human CD28, human 4-1BB, and human CD3ζ intracellular T cell signaling domains |
| SEQ ID NO: 11 (h139Ab-hCD28Z) | human antibody 139 | Human CD28 extracellular hinge and transmembrane domains<br>Human CD28 and human CD3ζ intracellular T cell signaling domains |

The invention also provides related nucleic acids, recombinant expression vectors, host cells, populations of cells, antibodies, or antigen binding portions thereof, and pharmaceutical compositions relating to the CARs of the invention.

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the invention are functional variants of the inventive CARs described herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the inventive CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gln, Ser, Thr, Tyr, etc.), an amino acid with a beta-branched side-chain substituted for another amino acid with a beta-branched side-chain (e.g., Ile, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs of embodiments of the invention (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a host, or treat or prevent disease in a host, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs of embodiments of the invention (including functional portions and functional variants of the invention) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2- amino-2-norbornane)-carboxylic acid, α,γ-diaminobutyric acid, α,β-diaminopropionic acid, homophenylalanine, and α-tert-butylglycine.

The CARs of embodiments of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs of embodiments of the invention (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., *Fmoc Solid Phase Peptide Synthesis*, Oxford University Press, Oxford, United Kingdom, 2000; *Peptide and Protein Drug Analysis*, ed. Reid, R., Marcel Dekker, Inc., 2000; *Epitope Mapping*, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the CARs of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive CARs can be synthetic, recombinant, isolated, and/or purified.

An embodiment of the invention further provides an antibody, or antigen binding portion thereof, which specifically binds to an epitope of the CARs of the invention. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive CAR.

Methods of testing antibodies for the ability to bind to any functional portion of the inventive CAR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1).

Phage display furthermore can be used to generate an antibody. In this regard, phage libraries encoding antigen-binding variable (V) domains of antibodies can be generated using standard molecular biology and recombinant DNA techniques (see, e.g., Sambrook et al., supra, and Ausubel et al., supra). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235, 959-973 (1994).

An embodiment of the invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which is a truncated Fab fragment including the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Further provided by an embodiment of the invention is a nucleic acid comprising a nucleotide sequence encoding any of the CARs described herein (including functional portions and functional variants thereof). An embodiment of the invention provides a nucleic acid comprising a nucleotide sequence encoding an antigen binding domain of human antibody 139 comprising SEQ ID NO: 12 (encoding the leader sequence, light chain variable region of human antibody 139, linker peptide, and heavy chain variable region of human antibody 139). In this regard, an embodiment of the invention provides nucleic acids comprising, consisting of, or consisting essentially of the nucleotide sequences of Table 2:

TABLE 2

| Sequence | scFv | Further Components |
|---|---|---|
| SEQ ID NO: 13 (h139Ab-hCD828BBZ) | human antibody 139 | Human CD8 extracellular hinge and transmembrane domains Human CD28, human 4-1BB, and human CD3ζ intracellular T cell signaling domains |
| SEQ ID NO: 14 (h139Ab-hCD28Z) | human antibody 139 | Human CD28 extracellular hinge and transmembrane domains Human CD28 and human CD3ζ intracellular T cell signaling domains |

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

The nucleic acids of an embodiment of the invention may be recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-$N^2$-carboxypropyl)uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment of the invention also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids of the invention can be incorporated into a recombinant expression vector. In this regard, an embodiment of the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences, Glen Burnie, Md.), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM, and pMAMneo (Clontech). The recombinant expression vector may be a viral vector, e.g., a retroviral vector.

A number of transfection techniques are generally known in the art (see, e.g., Graham et al., *Virology,* 52: 456-467 (1973); Sambrook et al., supra; Davis et al., *Basic Methods in Molecular Biology*, Elsevier (1986); and Chu et al., *Gene,* 13: 97 (1981). Transfection methods include calcium phosphate co-precipitation (see, e.g., Graham et al., supra), direct micro injection into cultured cells (see, e.g., Capecchi, *Cell,* 22: 479-488 (1980)), electroporation (see, e.g., Shigekawa et al., *BioTechniques,* 6: 742-751 (1988)), liposome mediated gene transfer (see, e.g., Mannino et al., *BioTechniques,* 6: 682-690 (1988)), lipid mediated transduction (see, e.g., Feigner et al., *Proc. Natl. Acad. Sci. USA,* 84: 7413-7417 (1987)), and nucleic acid delivery using high velocity microprojectiles (see, e.g., Klein et al., *Nature,* 327: 70-73 (1987)).

In an embodiment, the recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2μ plasmid, λ, SV40, bovine papilloma virus, and the like.

The recombinant expression vector may comprise regulatory sequences, such as transcription and translation initiation and termination codons, which are specific to the type of host (e.g., bacterium, fungus, plant, or animal) into which the vector is to be introduced, as appropriate, and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or normative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews,* Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Included in the scope of the invention are conjugates, e.g., bioconjugates, comprising any of the inventive CARs (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5α cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., $Th_1$ and $Th_2$ cells, $CD8^+$ T cells (e.g., cytotoxic T cells), tumor infiltrating cells, memory T cells, naïve T cells, and the like. The T cell may be a $CD8^+$ T cell or a $CD4^+$ T cell.

Also provided by an embodiment of the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), all of which are collectively referred to as "inventive CAR materials" hereinafter, can be isolated and/or purified. The term "isolated" as used herein means having been removed from its natural environment. The term "purified" or "isolated" does not require absolute purity or isolation; rather, it is intended as a relative term. Thus, for example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

The inventive CAR materials can be formulated into a composition, such as a pharmaceutical composition. In this regard, an embodiment of the invention provides a pharmaceutical composition comprising any of the CARs, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive CAR materials can comprise more than one inventive CAR material, e.g., a CAR and a nucleic acid, or two or more different CARs. Alternatively, the pharmaceutical composition can comprise an inventive CAR material in combination with other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In a preferred embodiment, the pharmaceutical composition comprises the inventive host cell or populations thereof.

The inventive CAR materials can be provided in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

With respect to pharmaceutical compositions, the pharmaceutically acceptable carrier can be any of those conventionally used and is limited only by chemico-physical considerations, such as solubility and lack of reactivity with the active agent(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive CAR material, as well as by the particular method used to administer the inventive CAR material. Accordingly, there are a variety of suitable formulations of the pharmaceutical composition of the invention. Preservatives may be used. Suitable preservatives may include, for example, methylparaben, propylparaben, sodium benzoate, and benzalkonium chloride. A mixture of two or more preservatives optionally may be used. The preservative or mixtures thereof are typically present in an amount of about 0.0001% to about 2% by weight of the total composition.

Suitable buffering agents may include, for example, citric acid, sodium citrate, phosphoric acid, potassium phosphate, and various other acids and salts. A mixture of two or more buffering agents optionally may be used. The buffering agent or mixtures thereof are typically present in an amount of about 0.001% to about 4% by weight of the total composition.

The concentration of inventive CAR material in the pharmaceutical formulations can vary, e.g., from less than about 1%, usually at or at least about 10%, to as much as about 20% to about 50% or more by weight, and can be selected primarily by fluid volumes, and viscosities, in accordance with the particular mode of administration selected.

Methods for preparing administrable (e.g., parenterally administrable) compositions are known or apparent to those skilled in the art and are described in more detail in, for example, *Remington: The Science and Practice of Pharmacy*, Lippincott Williams & Wilkins; 21st ed. (May 1, 2005).

The following formulations for oral, aerosol, parenteral (e.g., subcutaneous, intravenous, intraarterial, intramuscular, intradermal, interperitoneal, and intrathecal), and topical administration are merely exemplary and are in no way limiting. More than one route can be used to administer the inventive CAR materials, and in certain instances, a particular route can provide a more immediate and more effective response than another route.

Formulations suitable for oral administration can comprise or consist of (a) liquid solutions, such as an effective amount of the inventive CAR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard or softshelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive CAR material in a flavor, usually sucrose and acacia or tragacanth, as well as pastilles comprising the inventive CAR material in an inert base, such as gelatin and glycerin, or sucrose and acacia, emulsions, gels, and the like containing, in addition to, such excipients as are known in the art.

Formulations suitable for parenteral administration include aqueous and nonaqueous isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The inventive CAR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1,3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain, for example, from about 0.5% to about 25% by weight of the inventive CAR material in solution. Preservatives and buffers may be used. In order to minimize or eliminate irritation at the site of injection, such compositions may contain one or more nonionic surfactants having, for example, a hydrophile-lipophile balance (HLB) of from about 12 to about 17. The quantity of surfactant in such formulations will typically range, for example, from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with an embodiment of the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations, including those that are useful for transdermal drug release, are well known to those of skill in the art and are suitable in the context of embodiments of the invention for application to skin. The inventive CAR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

An "effective amount" or "an amount effective to treat" refers to a dose that is adequate to prevent or treat cancer in an individual. Amounts effective for a therapeutic or prophylactic use will depend on, for example, the stage and severity of the disease or disorder being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various diseases or disorders could require prolonged treatment involving multiple administrations, perhaps using the inventive CAR materials in each or various rounds of administration. By way of example and not intending to limit the invention, the dose of the inventive CAR material can be about 0.001 to about 1000 mg/kg body weight of the subject being treated/day, from about 0.01 to about 10 mg/kg body weight/day, about 0.01 mg to about 1 mg/kg body weight/day. When the inventive CAR material is a host cell, an exemplary dose of host cells may be a minimum of about one million cells (1 mg cells/dose). When the inventive CAR material is a nucleic acid packaged in a virus, an exemplary dose of virus may be about 1 ng/dose.

For purposes of the invention, the amount or dose of the inventive CAR material administered should be sufficient to effect a therapeutic or prophylactic response in the subject or animal over a reasonable time frame. For example, the dose of the inventive CAR material should be sufficient to bind to antigen, or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the animal (e.g., human), as well as the body weight of the animal (e.g., human) to be treated.

For purposes of the invention, an assay, which comprises, for example, comparing the extent to which target cells are lysed and/or IFN-γ is secreted by T cells expressing the inventive CAR upon administration of a given dose of such T cells to a mammal, among a set of mammals of which is each given a different dose of the T cells, could be used to determine a starting dose to be administered to a mammal. The extent to which target cells are lysed and/or IFN-γ is secreted upon administration of a certain dose can be assayed by methods known in the art.

In addition to the aforedescribed pharmaceutical compositions, the inventive CAR materials can be formulated as inclusion complexes, such as cyclodextrin inclusion complexes, or liposomes. Liposomes can serve to target the inventive CAR materials to a particular tissue. Liposomes also can be used to increase the half-life of the inventive CAR materials. Many methods are available for preparing liposomes, as described in, for example, Szoka et al., *Ann. Rev. Biophys. Bioeng.*, 9, 467 (1980) and U.S. Pat. Nos. 4,235,871, 4,501,728, 4,837,028, and 5,019,369.

The delivery systems useful in the context of embodiments of the invention may include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention.

Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

One of ordinary skill in the art will readily appreciate that the inventive CAR materials of the invention can be modified in any number of ways, such that the therapeutic or prophylactic efficacy of the inventive CAR materials is increased through the modification. For instance, the inventive CAR materials can be conjugated either directly or indirectly through a linker to a targeting moiety. The practice of conjugating compounds, e.g., inventive CAR materials, to targeting moieties is known in the art. See, for instance, Wadwa et al., *J. Drug Targeting* 3: 111 (1995) and U.S. Pat. No. 5,087,616.

Alternatively, the inventive CAR materials can be modified into a depot form, such that the manner in which the inventive CAR materials is released into the body to which it is administered is controlled with respect to time and location within the body (see, for example, U.S. Pat. No. 4,450,150). Depot forms of inventive CAR materials can be, for example, an implantable composition comprising the inventive CAR materials and a porous or non-porous material, such as a polymer, wherein the inventive CAR materials are encapsulated by or diffused throughout the material and/or degradation of the non-porous material. The depot is then implanted into the desired location within the body and the inventive CAR materials are released from the implant at a predetermined rate.

When the inventive CAR materials are administered with one or more additional therapeutic agents, one or more additional therapeutic agents can be coadministered to the mammal. By "coadministering" is meant administering one or more additional therapeutic agents and the inventive CAR materials sufficiently close in time such that the inventive CAR materials can enhance the effect of one or more additional therapeutic agents, or vice versa. In this regard, the inventive CAR materials can be administered first and the one or more additional therapeutic agents can be administered second, or vice versa. Alternatively, the inventive CAR materials and the one or more additional therapeutic agents can be administered simultaneously. An exemplary therapeutic agent that can be co-administered with the CAR materials is IL-2. It is believed that IL-2 enhances the therapeutic effect of the inventive CAR materials. For purposes of the inventive methods, wherein host cells or populations of cells are administered to the host, the cells can be cells that are allogeneic or autologous to the host.

It is contemplated that the inventive pharmaceutical compositions, CARs, nucleic acids, recombinant expression vectors, host cells, or populations of cells can be used in methods of treating or preventing a disease in a host. Without being bound to a particular theory or mechanism, the inventive CARs have biological activity, e.g., ability to recognize antigen, e.g., EGFRvIII, such that the CAR when expressed by a cell is able to mediate an immune response against the cell expressing the antigen, e.g., EGFRvIII, for which the CAR is specific. In this regard, an embodiment of the invention provides a method of treating or preventing cancer in a host, comprising administering to the host the CARs, the nucleic acids, the recombinant expression vectors, the host cells, the population of cells, the antibodies and/or the antigen binding portions thereof, and/or the pharmaceutical compositions of the invention in an amount effective to treat or prevent cancer in the host.

An embodiment of the invention further comprises lymphodepleting the host prior to administering the inventive CAR materials. Examples of lymphodepletion include, but may not be limited to, nonmyeloablative lymphodepleting chemotherapy, myeloablative lymphodepleting chemotherapy, total body irradiation, etc.

For purposes of the inventive methods, wherein host cells or populations of cells are administered, the cells can be cells that are allogeneic or autologous to the host. Preferably, the cells are autologous to the host.

The host referred to herein can be any host. The host may be a mammal. As used herein, the term "mammal" refers to any mammal, including, but not limited to, mammals of the order Rodentia, such as mice and hamsters, and mammals of the order Logomorpha, such as rabbits. The mammals may be from the order Carnivora, including Felines (cats) and Canines (dogs). The mammals may be from the order Artiodactyla, including Bovines (cows) and Swines (pigs) or of the order Perssodactyla, including Equines (horses). The mammals may be of the order Primates, Ceboids, or Simoids (monkeys) or of the order Anthropoids (humans and apes). Preferably, the mammal is a human.

With respect to the inventive methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma), lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, and ureter cancer. Preferably, the cancer is glioma (e.g., ependymoma, astrocytoma, oligodendroglioma, and oligoastrocytoma), more preferably, glioblastoma multiforme (GBM) (also known as glioblastoma, astrocytoma grade IV, and grade IV astrocytoma). Preferably, the cancer is characterized by the expression of EGFRvIII.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment of the invention provides a use of the inventive CARs, nucleic acids, recombinant expression vectors, host cells, populations of cells, antibodies, or antigen binding portions thereof, or pharmaceutical compositions, for the treatment or prevention of cancer in a host.

Another embodiment of the invention provides a method of detecting the presence of cancer in a host, comprising: (a) contacting a sample comprising one or more cells from the host with the CARs, the nucleic acids, the recombinant expression vectors, the host cells, the population of cells, the antibodies, and/or the antigen binding portions thereof of the invention, thereby forming a complex, (b) detecting the complex, wherein detection of the complex is indicative of the presence of cancer in the host.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the inventive method of detecting the presence of cancer in a host, the sample comprising cells of the host can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the host, e.g., the cells of any organ or tissue, including blood cells or endothelial cells.

For purposes of the inventive detecting method, the contacting can take place in vitro or in vivo with respect to the host. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

Methods of testing a CAR for the ability to recognize target cells and for antigen specificity are known in the art. For instance, Clay et al., *J. Immunol.*, 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytoxicity, as described in Zhao et al., *J. Immunol.*, 174: 4415-4423 (2005).

The following examples further illustrate the invention but, of course, should not be construed as in any way limiting its scope.

EXAMPLE 1

This example demonstrates that a CAR comprising SEQ ID NO: 10 (h139Ab-hCD828BBZ) or SEQ ID NO: 11 (h139Ab-hCD28Z) produces IFN-gamma following co-culture with EGFRvIII engineered target cell lines.

Chimeric antigen receptors targeting EGFRvIII were produced by combining single chain antibody sequences from 7 different anti-EGFRvIII antibodies to the T cell signaling domains of CD28 and CD3zeta. A total of 9 different constructs were assembled (in 2 constructs the order of the VL and VH were switched) based on murine antibodies 3C10, MR-1, Y10, L8A4, and human antibodies 131, 139, and 13.1.2, which were inserted into the γ-retroviral vector MSGV1. The expression of each construct was tested by transducing peripheral blood lymphocytes (PBL) and fluorescence-activated cell sorting (FACS) analysis using an anti-Fab specific reagent (or protein L in later experiments). Three of the nine vectors constructed reproducible demonstrated CAR expression in transduced PBL, specifically those CARs based on antibodies 3C10, L8A4, and 139 (SEQ ID NO: 11) were shown to have cell surface staining in transduced PBL.

To test the biological activity of these 3 anti-EGFRvIII CAR constructs, γ-retroviral vector supernatant was produced and used to transduce PBL, which were co-cultured with EGFRvIII-expressing target cell lines. In order to develop an in vitro system to evaluate potential EGFRvIII targeting vectors, an appropriate target cell line was established because no known glioblastoma cell lines express EGFRvIII. The wild type EGFR gene was obtained from commercial sources and the vIII form was constructed by polymerase chain reaction (PCR) and inserted into a retroviral vector, which coexpressed a NeoR gene. Several cell lines (NIH-3T3, BHK, HEK-293GP, U87, and U251) were transduced and selected and EGFRvIII expression was determined by a viii specific antibody.

Specific IFN-gamma production was demonstrated for all three constructs by co-culture with EGFRvIII engineered established cell lines (FIGS. 3A, 3B, and 3C, representative data for co-cultures with NIH-3T3, BHK, and 293GP derived lines). BHK cells (BHK), EGFR transduced BHK (BHK-EGFRwt), EGFRvIII transduced BHK (BHK-EGFR vIII), 3T3 cells (3T3UT), EGFR transduced 3T3 (3T3-EGFRwt), EGFRvIII transduced 3T3 (3T3-EGFRvIII), 293GP cells (293GPUT), or EGFRvIII transduced 293GP (293GP-EGFRvIII), were co-cultured with the indicated CAR-transduced PBL (or untransduced (UT) PBL as controls) and IFN-gamma levels determined (values are IFN-gamma in pg/ml following overnight co-culture). In these co-culture assays, all three CARs 3C10, L8A4 and 139 yielded specific IFN-γ production when exposed to EGFRvIII expressing target cells, but not cells engineered to over express the wild type EGFR gene. Based on the observation that the 139 CAR was slightly more reactive and is of human origin, and therefore less likely to be immunogenic in patients, all subsequent assays were done with the 139 scFv-based CAR construct (SEQ ID NO: 11). T cells from two donors that were transduced with the 139-CAR were sorted into CD8 and CD4 T cell populations and independently tested for reactivity (FIGS. 4A (Donor 2) and 4B (Donor 3)). Both CD4 and CD8 T cells specifically produced IFN-γ in co-culture with EGFRvIII target cells.

The addition of T cell signaling elements from the 41BB co-stimulatory molecule can enhance the survival of CAR engineered T cells. A new construct was assembled using signaling domains from CD28-41BB-CD3zeta (SEQ ID NO: 13) and compared to the original CD28-CD3zeta construct (SEQ ID NO: 14). While detection of the 28BBZ CAR vector construction by FACS was less than the 28Z construct, the transduced T cells were equally reactive against EGFRvIII expressing targets. T cells were transduced with these vectors and control vectors (GFP or the Her2/neu CAR) and co-cultured with engineered glioblastoma cell lines and glioblastoma multiforme tumor stem cell (GBM-TSC) lines (Tables 3A and 3B). Established glioblastoma lines U87 and U251 were engineered to express a control GFP gene, the wild type EGFR gene (EGFRwt), or the EGFRvIII gene (EGFRvIII). These target cells or GBM-TSC lines 308, 822, and 1228 were co-cultured with T cells transduced with the EGFRvIII-CAR vectors containing CD28-CD3zeta (139-28Z) (SEQ ID NO: 14) or CD28-41BB-CD3zeta (139-BBZ; h139Ab-hCD828BBZ) (SEQ ID NO: 13) signaling domains. IFN-γ levels were determined (values are IFN-γ in pg/ml following overnight co-culture with glioblastoma cell lines engineered to express EGFRvIII). Additional T cell controls included UT-untransduced PBL, GFP-GFP vector transduced PBL, and a Her2/neu specific CAR. Biological activity, as determined by IFN-γ release (Table 3A and 3B), demonstrated that the two different vector-transduced T cells were equally reactive against EGFRvIII expressing glioma cell lines U87 and U251.

TABLE 3A

| | Effector T-cell | | | | | |
|---|---|---|---|---|---|---|
| | U87 Cells (IFN-γ, pg/ml) | | | U251 Cells (IFN-γ, pg/ml) | | |
| | GFP | EGFR wt | EGFRvIII | UT | EGFR wt | EGFRvIII |
| GFP | 389 | 236 | 339 | 0 | 0 | 0 |
| 139-28Z | 451 | 561 | 1797 | 0 | 0 | 2743 |
| 139-28BB2 | 460 | 499 | 2117 | 0 | 0 | 1820 |
| ERBB2 | 1061 | 671 | 932 | 1195 | 2201 | 2692 |

TABLE 3B

| | UT | GFP | 139-28Z | 139-BBZ | HER2/Neu |
|---|---|---|---|---|---|
| GBM-TSC 308 | 0 | 35 | 987 | 1123 | 578 |
| GBM-TSC 822 | 0 | 95 | 1683 | 2267 | 372 |
| GBM-TSC 1228 | 0 | 0 | 1387 | 1493 | 371 |

EXAMPLE 2

This example demonstrates that a CAR comprising SEQ ID NO: 10 (h139Ab-hCD828BBZ) or SEQ ID NO: 11 (h139Ab-hCD28Z) specifically lyses cell lines engineered to express the mutant EGFRvIII.

The ability of EGFRvIII CAR engineered T cells to lyse target cells in a standard $^{51}$Cr-release assay was next determined (FIGS. 1A-D and 2A-D).

Untransduced (UnTd) PBL or PBL transduced with control GFP vector (GFP), 139-28Z CAR (vIII-28Z) (encoding SEQ ID NO: 11), or 139-28BBZ (vIII-BBZ) (encoding SEQ ID NO: 10) were co-cultured for four hours with $^{51}$Cr labeled target tumor cell lines (FIGS. 1A-1D: parent U87, GFP, wild type EGFR, or EGFRvIII engineered).

Untransduced (UnTd) PBL or PBL transduced with control GFP vector (GFP), anti-ERBB2 CAR (ERBB2), 139-28Z CAR (vIII-28Z) (encoding SEQ ID NO: 11) or 139-28BBZ (vIII-BBZ) (encoding SEQ ID NO: 10) were co-cultured for four hours with $^{51}$Cr labeled target tumor cell lines (FIGS. 2A-2D: parent U251, GFP, wild type EGFR, or EGFRvIII engineered).

In the experiments of FIGS. 1A-1D and 2A-2D, specific lysis of tumor cells was measured at the given E:T ratio using the formula: [(specific release-spontaneous release)/total release-spontaneous release)]. As shown in FIGS. 1A-1D and 2A-D, both vectors specifically lysed only cell lines engineered to express the mutant EGFRvIII and not control or wild-type EGFR engineered cell lines.

EXAMPLE 3

This example demonstrates that an anti-EGFRvIII CAR (SEQ ID NO: 10 (h139Ab-hCD828BBZ)) produces IFN-gamma following co-culture with tumor stem cell (TSC) lines.

By detailed molecular analysis of many different classes of cancer cell lines, it has now been demonstrated that established cancer cell lines often do not mirror the molecular characteristics of primary human cancers and this is the case for glioma lines. An alternative to the use of established glioma cell lines is the analysis of tumor stem cell (TSC) lines. The TSC paradigm proposes that a subpopulation of cells exist in cancer that give rise to all the cells in a differentiated tumor. It has been demonstrated that in situ glioma cells share properties not found in glioma cell lines, and harbor features consistent with tumor stem cells. It was further demonstrated that marked phenotypic and genotypic differences exist between primary human tumor-derived TSCs and their matched glioma cell lines. TSCs derived directly from primary glioblastomas harbor extensive similarities to normal neural stem cells and recapitulate the genotype, gene expression patterns, and in vivo biology of human glioblastomas. These findings suggest that glioma-derived TSCs may be a more reliable model than many commonly utilized glioma cell lines for understanding the biology of primary human tumors.

Therefore three TSC lines were analyzed for the presence of EGFRvIII and demonstrated by RT-PCR that EGFRvIII is expressed in these lines. PBL from two donors (Effector I and Effector II) were then engineered with the anti-EGFRvIII CAR vector (expressing SEQ ID NO: 10 (h139Ab-hCD828BBZ)) and co-cultured with glioma TSC lines and control EGFRvIII expressing cell lines. Five post-transduction PBL were co-cultured with glioma TSC lines or cell line U251 that had been engineered to express wild type EGFR, or EGFRvIII. Untransduced (UT) cells and GFP transduced cells served as negative controls and an anti-ERBB2 CAR served as a positive control in all co-cultures. As shown in FIGS. 5A and 5B, EGFRvIII CAR engineered T cells demonstrated specific recognition of the U251 EGFRvIII, when compared to the U251 EGFR wild type gene-engineered cells, and recognized all three glioma TSC lines tested (308, 822, and 1228). These results further support the use of EGFRvIII CAR engineered T cells as a potential immunotherapy for glioma patients.

EXAMPLE 4

This example demonstrates that CAR-engineered T-cells retain reactivity following expansion of the number of T-cells.

The 139-28BBZ (h139Ab-hCD828BBZ) vector was used to transduce PBL from two glioblastoma patients, as well as a healthy donor and tested for expression and reactivity. Transduced cells were co-cultured with EGFRvIII-engineered U87 cells and then assayed by intracellular cytokine staining. Engineered T cells from the patients and the healthy donor demonstrated specific IFN-γ production in both CD8+ and CD8− (presumably CD4+) CD3+ T cells (7.8%-16.2% IFN-γ+, vs. >0.36% against the control U87 line). Transduction efficiency was also similar between the glioblastoma patient T cells and the healthy donor. If large numbers of T cells (>1×10$^9$) are required for future clinical applications, these can be obtained via, for example, a 14-day rapid expansion protocol (REP) (Riddell et al., *J. Immunol. Methods*, 128: 189-201 (1990)). To verify that 139-28BBZ (h139Ab-hCD828BBZ) CAR transduced T cells could be expanded to numbers sufficient for patient treatment, and still maintain reactivity, these T cells were subject to REP and retested. The 139-CAR transduced T cells retained their ability to specifically produce IFN-γ as shown in Table 4.

TABLE 4

| | IFN-γ Elispot per 1 × 10$^6$ cells | | | | | |
|---|---|---|---|---|---|---|
| | Donor 6 | | GBM-1 | | GBM-2 | |
| | UT | CAR | UT | CAR | UT | CAR |
| U87 | 0 | <500 | 0 | 0 | 0 | <500 |
| vIII | 0 | >5500 | 0 | >5500 | 0 | >5500 |
| PHA | 5000 | 3500 | 2800 | 1500 | 4500 | 5000 |

EXAMPLE 5

This example demonstrates the production of a producer cell clone useful for producing viral vector supernatant for transducing cells.

Using the 139-28BBZ (h139Ab-hCD828BBZ) EGFRvIII CAR construct, a PG13 γ-retroviral vector producer cell clone was produced under conditions that meet U.S. Food and Drug Administration (FDA) guidelines for human gene therapy clinical trials. One cell clone (clone F10) was used to produce 18 L of viral vector supernatant in 6 harvests collected over 4 days. Each harvest was used to transduce donor PBL and the gene transfer efficiency and biologic activity were determined. All harvests produced biologically active supernatant based on the ability of transduced T cells to express the CAR and to specifically recognize EGFRvIII expressing cell lines. Harvest 1 was slightly less reactive than harvest 2-6 in this assay. To test for possible toxicity against normal human tissues, a pool of harvests 3 and 4 was used to transduce a different donor and these transduced T cells were co-cultured with seven different primary human adult and neonatal-cell cultures of epithelial, endothelial, and fibroblast origin. As determined by IFN-γ production, there was no reactivity of the EGFRvIII CAR transduced T cells with any primary human cell culture tested.

EXAMPLE 6

This example demonstrates a method of treating or preventing cancer in a human patient comprising administering to the patient a CAR comprising SEQ ID NO: 10 (h139Ab-hCD828BBZ).

Eligibility

Eligible patients have histologically proven glioblastoma expressing EGFRvIII as determined by immunohistochemistry (IHC); failed prior standard treatment with radiotherapy with or without chemotherapy; a Karnofsky score greater than or equal to 60%; cardiac, pulmonary, and laboratory parameters within acceptable limits.

Study Design:

The study is conducted using a Phase I/II design. Patients are accrued to both the Phase I and Phase II portion of the trial in two groups: 1) patients with recurrent malignant glioma requiring steroid use at the start of treatment or 2) patients with recurrent malignant glioma not requiring steroid use at the start of treatment. Once the maximum tolerated dose is determined for each individual group in the phase I portion of the trial, the study proceeds to the phase II portion. Patients are again accrued to the same two groups. For each of the two groups evaluated, the study is conducted using a single stage phase II design.

Patients receive a non-myeloablative but lymphocyte depleting preparative regimen including cyclophosphamide and fludarabine followed by intravenous infusion of ex vivo tumor reactive, EGFRvIII CAR gene-transduced PBMC, plus intravenous (IV) aldesleukin (720,000 IU/kg q8h for a maximum of 15 doses). Patients undergo complete evaluation of tumor with physical and neurological examination, MRI of the brain with and without gadolinium, and clinical laboratory evaluation four weeks (+/−7 days) after completion of treatment. If the patient has stable disease or tumor shrinkage, repeat complete evaluations are performed every 1 month (+/−7 days. After the first year, patients continuing to respond continue to be followed with this evaluation every 2 months (+/−7 days) as appropriate.

Cell Preparation:

PBMC are obtained by leukapheresis (approximately $1 \times 10^{10}$ cells). Whole PBMC are cultured in the presence of anti-CD3 (OKT3) and aldesleukin in order to stimulate T-cell growth, Transduction is initiated by exposure of approximately $1 \times 10^7$ to $5 \times 10^8$ cells to supernatant containing the anti-EGFRvIII CAR retroviral vector. These transduced cells are expanded and tested for their anti-tumor activity. Successful CAR gene transfer is determined by FACS analysis for the CAR protein and anti-tumor reactivity is tested by cytokine release as measured on EGFRvIII expressing cells. Successful CAR gene transfer for each transduced PBL population is defined as >10% CAR positive cells and for biological activity, gamma-interferon secretion must be at least 200 pg/ml and twice the background level.

Anti-EGVRvIII CAR Transduced PBL:

The PBL are transduced with retroviral supernatant containing the chimeric anti-EGFRvIII CAR. The retroviral vector supernatant (PG13-139-F10) encoding a chimeric antigen receptor (CAR) directed against the antigen, EGFRvIII, is prepared and preserved following current good manufacturing practice (cGMP) conditions. The retroviral vector utilizes the MSGV1 retroviral vector backbone and includes 4,032 bps including the 5' LTR from the murine stem cell virus (promoter), packaging signal including the splicing donor (SD) and splicing acceptor sites, human anti-EGFRvIII scFv-based (mAb 139) CAR protein containing a signal peptide signal (human GM-CSFR), 139 light chain variable region, linker peptide, 139 heavy chain variable region, CD8 (hinge, transmembrane), CD28 (cytoplasmic region), 4-1BB (cytoplasmic region) and TCR zeta (cytoplasmic region), followed by the murine stem cell virus 3'LTR. The vector comprises nucleotide sequence SEQ ID NO: 13, which encodes amino acid sequence SEQ ID NO: 10. The physical titer is determined by RNA dot blot according to sponsor certificate. The supernate is stored at SBVPF upon the completion of production at −80° C. with around-the-clock temperature monitoring. Upon request, supernatant is delivered on dry ice to be used in in vitro transduction. There is no re-use of the same unit of supernate for different patients. Retroviral titer has been shown to be stable after immediate thawing and immediate administration (coating the tissue culture wells previously coated with Retronectin). Handling of the vector follows the guidelines of Biosafety Level-2 (BSL-2).

Phase I—Dose Escalation:

The protocol begins with a phase 1 dose escalation design, with eight cohorts and with two different groups (one for patients receiving steroids at the time of treatment and one for patients not on steroids). Each group is treated as a totally separate dose escalation trial.

Initially, the protocol enrolls 1 patient in each of the first 3 dose cohorts unless that patient experiences a dose limiting toxicity (DLT). Following cohort 3, all subsequent cohorts proceed in a phase 1 dose escalation design, with 5 cohorts of The total number of EGFRvIII engineered cells transferred for each cohort is according to Table 5:

TABLE 5

| Dose Escalation Schedule | |
| --- | --- |
| Dose Level | Dose of Anti-EGFRvIII CAR T cells |
| Cohort 1 (group a & b) | $10^7$ |
| Cohort 2 (group a & b) | $3 \times 10^7$ |
| Cohort 3 (group a & b) | $10^8$ |
| Cohort 4 (group a & b) | $3 \times 10^8$ |

TABLE 5-continued

| Dose Escalation Schedule | |
| --- | --- |
| Dose Level | Dose of Anti-EGFRvIII CAR T cells |
| Cohort 5 (group a & b) | $10^9$ |
| Cohort 6 (group a & b) | $3 \times 10^9$ |
| Cohort 7 (group a & b) | $10^{10}$ |
| Cohort 8 (group a & b) | $3\text{-}6 \times 10^{10}$ |

Patients are enrolled sequentially, therefore enrollment does not proceed to a higher dose level until patients have been treated in the prior cohort. Patients, however, are dose-escalated to the next cohort within a given group independent of what is occurring in the other strata. If sufficient cells cannot be grown to meet the criteria for the assigned cohort, the patient is enrolled in the appropriate cohort for the number of cells infused.

In cohorts 1 through 3, if the patient experiences a DLT, five more patients would be treated at that dose to confirm that no greater than 1/6 patients have a DLT prior to proceeding to the next higher level. If a level with 2 or more DLTs in 3-6 patients has been identified, five additional patients are accrued at the next-lowest dose, for a total of 6, in order to further characterize the safety of the maximum tolerated dose prior to starting the phase II portion. If there are 1 or fewer DLTs in the first cohort, the study proceeds to the second cohort. If a dose limiting toxicity occurs in the first cohort, that cohort is expanded to n=6 patients. If two DLTs occur in the first cohort, the study is terminated.

In cohorts 4-8, should a single patient experience a dose limiting toxicity due to the cell infusion at a particular dose level, three more patients would be treated at that dose to confirm that no greater than 1/6 patients have a DLT prior to proceeding to the next higher level. If a level with 2 or more DLTs in 3-6 patients has been identified, three additional patients are accrued at the next-lowest dose, for a total of 6, in order to further characterize the safety of the maximum tolerated dose prior to starting the phase II portion.

The maximum tolerated cell dose is the highest dose at which ≤1 of 6 patients experienced a DLT or the highest dose level studied if DLTs are not observed at any of the three dose levels.

Prior to receiving the engineered PBL cells, all patients receive a nonmyeloablative, but lymphocyte depleting preparative regimen, including cyclophosphamide and fludarabine followed in one to four days by intravenous infusion of in vitro tumor reactive, EGFRvIII CAR gene-transduced PBL plus IV aldesleukin (720,000 IU/kg Oh for a maximum of 15 doses).

The maximum tolerated cell dose is the highest dose at which <1 of 6 patients experienced a DLT or the highest dose level studied if DLTs are not observed at any of the three dose levels.

Dose-limiting toxicity is defined as follows: Grade 2 or greater allergic reaction or reaction that involves bronchospasm or generalized urticaria; all grade 3 and 4 toxicities with the exception of: myelosuppression, defined as lymphopenia, neutropenia and thrombocytopenia; IL-2 expected toxicities; toxicities occurring within 24 hours post cell infusion (related to cell infusion) that are reversible to a grade 2 or less within 8 hours with two doses of acetaminophen (650 mg) or two doses of diphenhydramine (25 mg).

Treatment Schedule

The treatment schedule is set forth in Table 6:

TABLE 6

| Therapy | Day | | | | | | | | | | | |
|---|---|---|---|---|---|---|---|---|---|---|---|---|
| | −7 | −6 | −5 | −4 | −3 | −2 | −1 | 01 | 1 | 2 | 3 | 4 |
| Cyclophosphamide (60 mg/kg) | X | X | | | | | | | | | | |
| Fludarabine (25 mg/m$^2$) | | | X | X | X | X | X | | | | | |
| Anti-EGFRvIII CAR PBL | | | | | | | | X$^1$ | | | | |
| Aldesleukin | | | | | | | | X$^2$ | X | X | X | X |
| Filgrastim$^3$ (5 mcg/kg/day) | | | | | | | | | X | X | X | X |
| trimethoprim and sulfamethoxazole (TMP/SMX)$^4$ 160 mg/800 mg | X | X | X | X | X | X | X | X | X | X | X | X |
| Fluconazole$^5$ (400 mg po) | | | | | | | | | X | X | X | X |
| Valacyclovir po or Acyclovir IV$^6$ | | | | | | | | | X | X | X | X |

$^1$One to four days after the last dose of fludarabine
$^2$Initiate within 24 hours after cell infusion
$^3$Continue until neutrophils count >1 × 10$^9$/L for 3 consecutive days or >5 × 10$^9$/L.
$^4$The TMP/SMX schedule should be adjusted to QD three times per week (Monday, Wednesday, Friday) and continue for at least six months and until CD4 >200 × 2
$^5$Continue until ANC >1000/mm$^3$
$^6$In patients positive for HSV continue until ANC is greater than 1000/mm$^3$ Immunological Testing:

Apheresis is performed prior to, and 4-6 weeks after, the treatment. At other time points, patient peripheral blood lymphocytes (PBL) are obtained from whole blood by purification using centrifugation on a Ficoll cushion. Aliquots of these PBMC are 1) cryopreserved for immunological monitoring of cell function, 2) subjected to DNA and RNA extraction for PCR analysis of CAR and vector copy number estimation, and 3) lymphocytes are tested directly and following in vitro culture. Direct immunological monitoring includes quantifying T cells reactive with EGFRvIII by FACS analysis using CAR-specific staining. Ex vivo immunological assays include cytokine release by bulk PBL (+/− antigen stimulation) and by other experimental studies such as cytolysis if sufficient cells are available. If cell numbers are limiting, preference is given to the direct analysis of immunological activity. Immunological assays are standardized by the inclusion of 1) pre-infusion PBMC and 2) an aliquot of the engineered PBL cryopreserved at the time of infusion. In general, differences of 2 to 3 fold in these assays are indicative of true biologic differences.

Monitoring Gene Therapy Trials: Persistence and Replication-Competent Retrovirus (RCR):

Engineered cell survival: CAR and vector presence is quantitated in PBMC samples using established PCR techniques. Immunological monitoring using CAR-specific staining is used to augment PCR-based analysis. This provides data to estimate the in vivo survival of lymphocytes derived from the infused cells. In addition, measurement of CD4 and CD8 T-cells is conducted and studies of these T-cell subsets in the circulation are determined by using specific PCR assays capable of detecting the unique DNA sequence for each retroviral vector engineered T-cell.

Patients' blood samples are obtained and undergo analysis for detection of RCR by PCR prior to cell infusion and RCR PCR is performed at 3 and 6 months, and at one year post cell administration. Blood samples are archived annually thereafter if all previous testing has been negative with a brief clinical history. If a patient dies or develops neoplasms during this trial, efforts are made to assay a biopsy sample for RCR. If any post-treatment samples are positive, further analysis of the RCR and more extensive patient follow-up is undertaken, in consultation with the FDA. RCR PCR assays detect the GaLV envelop gene and are performed under contract by the National Gene Vector Laboratory at Indiana University The results of these tests are maintained by the contractor performing the RCR tests and by the National Cancer Institute (NCI) Surgery Branch research team.

Due to the nature of these studies, it is possible that expansion of specific T-cell clones is observed as tumor reactive T-cell proliferation in response to tumor antigens. Therefore, care is taken to track T-cell persistence both immunologically and molecularly. Blood samples (5-10 mL) for persistence of CAR transduced cells are obtained 1 month after cell infusion, then at 3, 6, 12 months, and then annually thereafter. If any patient shows a high level of persistence of CAR gene transduced cells at month 6 (by semi quantitative DNA-PCR using primers specific for vector sequences) the previously archived samples are subjected to techniques that would allow the identification of clonality of persisting CAR gene transduced cells. Such techniques may include T cell cloning or LAM-PCR 30. If a predominant or monoclonal T cell clone derived from CAR gene transduced cells is identified during the follow-up, the integration site and sequence are identified and subsequently analyzed against human genome database to determine whether the sequences are associated with any known human cancers. If a predominant integration site is observed, the T cell cloning or LAM-PCR test is used at an interval of no more than three months after the first observation to see if the clone persists or is transient. In all instances where monoclonality is persistent and particularly in instances where there is expansion of the clone, regardless of whether or not the sequence is known to be associated with a known human cancer, the subject should be monitored closely for signs of malignancy, so that treatment, if available, may be initiated early.

Post Treatment Evaluation (Follow-up)

Routine Follow up: Patients are evaluated 4 weeks (+/−7 days) after the initial treatment regimen (defined as the end of the last aldesleukin dose). If the patient has SD or tumor shrinkage, repeat complete evaluations are performed monthly (+/−7 days) for 12 months, and then every 1-2 months (+/−7 days) as appropriate.

The following evaluations are performed at each evaluation: I) Physical examination, including neurological examination and Karnofsky score; II) Chem 20: (Sodium (Na), Potassium (K), Chloride (Cl), Total CO2 (bicarbonate), Creatinine, Glucose, Urea nitrogen (BUN), Albumin, Calcium total, Magnesium total (Mg), Inorganic Phosphorus, Alkaline Phosphatase, ALT/GPT, AST/GOT, Total Bilirubin, Direct Bilirubin, LD, Total Protein, Total CK, Uric Acid), complete blood count and thyroid panel; III) CBC; IV) Toxicity assessment; V) MRI of the brain with and without gadolinium; and VI) Detection of RCR and persistence of CAR gene transduced cells: (as described above).

A 5 liter apheresis is performed at the first follow up visit only. Subsequently, 60 ml of blood is obtained at follow up visits (approximately monthly) for at least 3 months. Peripheral blood mononuclear cells are cryopreserved so that immunologic testing may be performed.

Long-term Follow Up of Patients Receiving Gene Transfer:

Physical examinations are performed and documented annually for 5 years following cell infusion to evaluate long-term safety. After 5 years, health status data are obtained from surviving patients via telephone contact or mailed questionnaires. The long term follow up period for retroviral vectors is 15 years.

Response Criteria:

As part of this trial, as well as to assist in the determination of tumor progression, all efforts are made to observe radiographic changes in the patient's tumors over time.

Measurable Disease: Bidimensionally contrast-enhancing lesions with clearly defined margins by MRI scan, with two perpendicular diameters of at least 10 mm, visible on two or more axial slices. Measurement of tumor around a cyst or surgical cavity represents a particularly difficult challenge. In general, such lesions should be considered nonmeasurable unless there is a nodular component measuring ≥10 mm in diameter. The cystic or surgical cavity should not be measured in determining response.

Non-Measurable but Evaluable Disease: Unidimensionally measurable lesions, masses with margins not clearly defined, or lesions with a multiple cystic component.

Non-Evaluable Disease: No definitive, measurable or evaluable tumor.

Measurable Lesions:

Complete Response (CR): Complete response requires all of the following: complete disappearance of all enhancing measurable and nonmeasurable disease sustained for at least 4 weeks; no new lesions; stable or improved nonenhancing (T2/FLAIR) lesions; and patient must be off corticosteroids or on physiologic replacement doses only, and stable or improved clinically. In the absence of a confirming scan 4 weeks later, this response is considered only stable disease.

Partial Response (PR): Partial response requires all of the following: ≥50% decrease, compared with baseline, in the sum of products of perpendicular diameters of all measurable enhancing lesions sustained for at least 4 weeks; no progression of nonmeasurable disease; no new lesions; stable or improved nonenhancing (T2/FLAIR) lesions on same or lower dose of corticosteroids compared with baseline scan; and patient must be on a corticosteroid dose not greater than the dose at time of baseline scan and is stable or improved clinically. In the absence of a confirming scan 4 weeks later, this response is considered only stable disease.

Stable: Stable disease occurs if the patient does not qualify for complete response, partial response, or progression and requires the following: stable nonenhancing (T2/FLAIR) lesions on same or lower dose of corticosteroids compared with baseline scan and clinically stable status. In the event that the corticosteroid dose was increased for new symptoms and signs without confirmation of disease progression on neuroimaging, and subsequent follow-up imaging shows that this increase in corticosteroids was required because of disease progression, the last scan considered to show stable disease is the scan obtained when the corticosteroid dose was equivalent to the baseline dose.

Progression: Progression is defined by any of the following: >25% increase in sum of the products of perpendicular diameters of enhancing lesions (compared to best response or with baseline if no decrease) on stable or increasing doses of corticosteroids; a significant increase in T2/FLAIR nonenhancing lesions on stable or increasing doses of corticosteroids compared with baseline scan or best response after initiation of therapy, not due to comorbid events; the appearance of any new lesions; clear progression of nonmeasurable lesions; or definite clinical deterioration not attributable to other causes apart from the tumor, or to decrease in corticosteroid dose. Failure to return for evaluation as a result of death or deteriorating condition should also be considered as progression. Patients with nonmeasurable enhancing disease whose lesions have significantly increased in size and become measurable (minimal bidirectional diameter of ≥10 mm and visible on at least two axial slices) are also be considered to have experienced progression. The transition from a nonmeasurable lesion to a measurable lesion resulting in progression can theoretically occur with relatively small increases in tumor size (eg, a 9×9 mm lesion [nonmeasurable] increasing to a 10×11 mm lesion [measurable]). Ideally, the change should be significant (>5 mm increase in maximal diameter or >25% increase in sum of the products of perpendicular diameters of enhancing lesions). In general, if there is doubt about whether the lesion has progressed, continued treatment and close follow-up evaluation help clarify whether there is true progression.

Evaluable Lesions:

Evaluable lesions are recorded at each evaluation. FLAIR or T2-weighted images should also be assessed as evaluable disease if appropriate.

The following scale is used to designate relative changes in MRI scans:

+3=disappearance of tumor (CR)
+2=definitely better (PR)
+1=possibly better
0=unchanged
−1=possibly worse
−2=definitely worse (PD)
−3=development of a new lesion (PD).

Definition of Response for Evaluable Lesions

Complete Response (CR): is defined as the circumstance when the MRI scan is ranked +3 and the tumor is no longer seen by neuroimaging, and the patient no longer requires steroids for control of tumor-induced cerebral edema.

Partial response (PR): is defined as a MRI scan ranked +2 provided that the patient has not had his/her dose of steroids increased since the last evaluation period.

Progression (P): is defined as the circumstance when the MRI scan is ranked −2 or −3, or the presence of a new lesion.

Stable disease (SD): is defined as the circumstance when the MRI scan shows no change or possible (−1 or +1) changes. Patients should be receiving stable or decreasing doses of steroids.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A chimeric antigen receptor (CAR) comprising an amino acid sequence selected from the group consisting of SEQ ID NOs: 10-11.

2. A pharmaceutical composition comprising the CAR of claim 1 and a pharmaceutically acceptable carrier.

* * * * *

SEQUENCE LISTING

```
<160> NUMBER OF SEQ ID NOS: 28

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asn
            20                  25                  30

Leu Ala Trp Tyr Gln Gln Lys Pro Gly Lys Ala Pro Lys Arg Leu Ile
        35                  40                  45

Tyr Ala Ala Ser Asn Leu Gln Ser Gly Val Pro Ser Arg Phe Thr Gly
    50                  55                  60

Ser Gly Ser Gly Thr Glu Phe Thr Leu Ile Val Ser Ser Leu Gln Pro
65                  70                  75                  80

Glu Asp Phe Ala Thr Tyr Tyr Cys Leu Gln His His Ser Tyr Pro Leu
                85                  90                  95

Thr Ser Gly Gly Gly Thr Lys Val Glu Ile Lys
            100                 105

<210> SEQ ID NO 2
<211> LENGTH: 116
<212> TYPE: PRT
<213> ORGANISM: Homo sapiens

<400> SEQUENCE: 2

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Asn Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gly Ser Ser Gly Trp Ser Glu Tyr Trp Gly Gln Gly Thr Leu Val
            100                 105                 110

Thr Val Ser Ser
            115
```

-continued

```
<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Arg Thr Gly Ser Thr Ser Gly Ser Gly Lys Pro Gly Ser Gly Glu Gly
1               5                   10                  15

Ser

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Met Val Leu Leu Val Thr Ser Leu Leu Cys Glu Leu Pro His Pro
1               5                   10                  15

Ala Phe Leu Leu Ile Pro
                20

<210> SEQ ID NO 5
<211> LENGTH: 262
<212> TYPE: PRT
<213> ORGANISM: Artificial Sequence
<220> FEATURE:
<223> OTHER INFORMATION: Synthetic

<400> SEQUENCE: 5

Met Val Leu Leu Val Thr Ser Leu Leu Cys Glu Leu Pro His Pro
1               5                   10                  15

Ala Phe Leu Leu Ile Pro Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Asn Leu Ala Trp Tyr Gln Lys Pro Gly Lys
        50                  55                  60

Ala Pro Lys Arg Leu Ile Tyr Ala Ala Ser Asn Leu Gln Ser Gly Val
65                  70                  75                  80

Pro Ser Arg Phe Thr Gly Ser Gly Thr Glu Phe Thr Leu Ile
                85                  90                  95

Val Ser Ser Leu Gln Pro Glu Asp Phe Ala Thr Tyr Tyr Cys Leu Gln
                100                 105                 110

His His Ser Tyr Pro Leu Thr Ser Gly Gly Thr Lys Val Glu Ile
            115                 120                 125

Lys Arg Thr Gly Ser Thr Ser Gly Ser Gly Lys Pro Gly Ser Gly Glu
            130                 135                 140

Gly Ser Glu Val Gln Val Leu Glu Ser Gly Gly Leu Val Gln Pro
145                 150                 155                 160

Gly Gly Ser Leu Arg Leu Ser Cys Ala Ala Ser Gly Phe Thr Phe Ser
                165                 170                 175

Ser Tyr Ala Met Ser Trp Val Arg Gln Ala Pro Gly Lys Gly Leu Glu
                180                 185                 190

Trp Val Ser Ala Ile Ser Gly Ser Gly Ser Thr Asn Tyr Ala Asp
                195                 200                 205
```

```
Ser Val Lys Gly Arg Phe Thr Ile Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Gly Ser Ser Gly Trp Ser Glu Tyr Trp Gly Gln Gly Thr
                245                 250                 255

Leu Val Thr Val Ser Ser
            260

<210> SEQ ID NO 6
<211> LENGTH: 83
<212> TYPE: PRT
<213> ORGANISM: Homo sapiens

<400> SEQUENCE: 6

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn

<210> SEQ ID NO 7
<211> LENGTH: 200
<212> TYPE: PRT
<213> ORGANISM: Homo sapiens

<400> SEQUENCE: 7

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser Arg Phe Ser Val Val Lys Arg
        35                  40                  45

Gly Arg Lys Lys Leu Leu Tyr Ile Phe Lys Gln Pro Phe Met Arg Pro
    50                  55                  60

Val Gln Thr Thr Gln Glu Glu Asp Gly Cys Ser Cys Arg Phe Pro Glu
65                  70                  75                  80

Glu Glu Glu Gly Gly Cys Glu Leu Arg Val Lys Phe Ser Arg Ser Ala
            85                  90                  95

Asp Ala Pro Ala Tyr Gln Gln Gly Gln Asn Gln Leu Tyr Asn Glu Leu
        100                 105                 110

Asn Leu Gly Arg Arg Glu Glu Tyr Asp Val Leu Asp Lys Arg Arg Gly
    115                 120                 125

Arg Asp Pro Glu Met Gly Gly Lys Pro Arg Arg Lys Asn Pro Gln Glu
130                 135                 140

Gly Leu Tyr Asn Glu Leu Gln Lys Asp Lys Met Ala Glu Ala Tyr Ser
145                 150                 155                 160

Glu Ile Gly Met Lys Gly Glu Arg Arg Arg Gly Lys Gly His Asp Gly
            165                 170                 175
```

```
Leu Tyr Gln Gly Leu Ser Thr Ala Thr Lys Asp Thr Tyr Asp Ala Leu
            180                 185                 190
His Met Gln Ala Leu Pro Pro Arg
        195                 200

<210> SEQ ID NO 8
<211> LENGTH: 106
<212> TYPE: PRT
<213> ORGANISM: Homo sapiens

<400> SEQUENCE: 8

Ile Glu Val Met Tyr Pro Pro Tyr Leu Asp Asn Glu Lys Ser Asn
1               5                   10                  15
Gly Thr Ile Ile His Val Lys Gly Lys His Leu Cys Pro Ser Pro Leu
            20                  25                  30
Phe Pro Gly Pro Ser Lys Pro Phe Trp Val Leu Val Val Val Gly Gly
        35                  40                  45
Val Leu Ala Cys Tyr Ser Leu Leu Val Thr Val Ala Phe Ile Ile Phe
    50                  55                  60
Trp Arg Ser Lys Arg Ser Arg Leu Leu His Ser Asp Tyr Met Asn Met
65                  70                  75                  80
Thr Pro Arg Arg Pro Gly Pro Thr Arg Lys His Tyr Gln Pro Tyr Ala
                85                  90                  95
Pro Pro Arg Asp Phe Ala Ala Tyr Arg Ser
            100                 105

<210> SEQ ID NO 9
<211> LENGTH: 112
<212> TYPE: PRT
<213> ORGANISM: Homo sapiens

<400> SEQUENCE: 9

Arg Val Lys Phe Ser Arg Ser Ala Asp Ala Pro Ala Tyr Gln Gln Gly
1               5                   10                  15
Gln Asn Gln Leu Tyr Asn Glu Leu Asn Leu Gly Arg Arg Glu Glu Tyr
            20                  25                  30
Asp Val Leu Asp Lys Arg Arg Gly Arg Asp Pro Glu Met Gly Gly Lys
        35                  40                  45
Pro Arg Arg Lys Asn Pro Gln Glu Gly Leu Tyr Asn Glu Leu Gln Lys
    50                  55                  60
Asp Lys Met Ala Glu Ala Tyr Ser Glu Ile Gly Met Lys Gly Glu Arg
65                  70                  75                  80
Arg Arg Gly Lys Gly His Asp Gly Leu Tyr Gln Gly Leu Ser Thr Ala
                85                  90                  95
Thr Lys Asp Thr Tyr Asp Ala Leu His Met Gln Ala Leu Pro Pro Arg
            100                 105                 110

<210> SEQ ID NO 10
<211> LENGTH: 548
<212> TYPE: PRT
<213> ORGANISM: Artificial Sequence
<220> FEATURE:
<223> OTHER INFORMATION: Synthetic

<400> SEQUENCE: 10

Met Val Leu Leu Val Thr Ser Leu Leu Leu Cys Glu Leu Pro His Pro
1               5                   10                  15
Ala Phe Leu Leu Ile Pro Asp Ile Gln Met Thr Gln Ser Pro Ser Ser
            20                  25                  30
```

```
Leu Ser Ala Ser Val Gly Asp Arg Val Thr Ile Thr Cys Arg Ala Ser
         35                  40                  45

Gln Gly Ile Arg Asn Asn Leu Ala Trp Tyr Gln Gln Lys Pro Gly Lys
 50                  55                  60

Ala Pro Lys Arg Leu Ile Tyr Ala Ala Ser Asn Leu Gln Ser Gly Val
 65                  70                  75                  80

Pro Ser Arg Phe Thr Gly Ser Gly Ser Gly Thr Glu Phe Thr Leu Ile
                 85                  90                  95

Val Ser Ser Leu Gln Pro Glu Asp Phe Ala Thr Tyr Tyr Cys Leu Gln
             100                 105                 110

His His Ser Tyr Pro Leu Thr Ser Gly Gly Thr Lys Val Glu Ile
         115                 120                 125

Lys Arg Thr Gly Ser Thr Ser Gly Ser Gly Lys Pro Gly Ser Gly Glu
     130                 135                 140

Gly Ser Glu Val Gln Val Leu Glu Ser Gly Gly Gly Leu Val Gln Pro
145                 150                 155                 160

Gly Gly Ser Leu Arg Leu Ser Cys Ala Ala Ser Gly Phe Thr Phe Ser
                 165                 170                 175

Ser Tyr Ala Met Ser Trp Val Arg Gln Ala Pro Gly Lys Gly Leu Glu
             180                 185                 190

Trp Val Ser Ala Ile Ser Gly Ser Gly Gly Ser Thr Asn Tyr Ala Asp
             195                 200                 205

Ser Val Lys Gly Arg Phe Thr Ile Ser Arg Asp Asn Ser Lys Asn Thr
     210                 215                 220

Leu Tyr Leu Gln Met Asn Ser Leu Arg Ala Glu Asp Thr Ala Val Tyr
225                 230                 235                 240

Tyr Cys Ala Gly Ser Gly Trp Ser Glu Tyr Trp Gly Gln Gly Thr
                 245                 250                 255

Leu Val Thr Val Ser Ser Ala Ala Phe Val Pro Val Phe Leu Pro
             260                 265                 270

Ala Lys Pro Thr Thr Thr Pro Ala Pro Arg Pro Pro Thr Pro Ala Pro
             275                 280                 285

Thr Ile Ala Ser Gln Pro Leu Ser Leu Arg Pro Glu Ala Cys Arg Pro
     290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                 325                 330                 335

Ser Leu Val Ile Thr Leu Tyr Cys Asn His Arg Asn Arg Ser Lys Arg
             340                 345                 350

Ser Arg Leu Leu His Ser Asp Tyr Met Asn Met Thr Pro Arg Arg Pro
     355                 360                 365

Gly Pro Thr Arg Lys His Tyr Gln Pro Tyr Ala Pro Pro Arg Asp Phe
     370                 375                 380

Ala Ala Tyr Arg Ser Arg Phe Ser Val Val Lys Arg Gly Arg Lys Lys
385                 390                 395                 400

Leu Leu Tyr Ile Phe Lys Gln Pro Phe Met Arg Pro Val Gln Thr Thr
                 405                 410                 415

Gln Glu Glu Asp Gly Cys Ser Cys Arg Phe Pro Glu Glu Glu Glu Gly
             420                 425                 430

Gly Cys Glu Leu Arg Val Lys Phe Ser Arg Ser Ala Asp Ala Pro Ala
     435                 440                 445
```

-continued

Tyr Gln Gly Gln Asn Gln Leu Tyr Asn Glu Leu Asn Leu Gly Arg
    450                 455                 460

Arg Glu Glu Tyr Asp Val Leu Asp Lys Arg Arg Gly Arg Asp Pro Glu
465                 470                 475                 480

Met Gly Gly Lys Pro Arg Arg Lys Asn Pro Gln Glu Gly Leu Tyr Asn
                485                 490                 495

Glu Leu Gln Lys Asp Lys Met Ala Glu Ala Tyr Ser Glu Ile Gly Met
            500                 505                 510

Lys Gly Glu Arg Arg Arg Gly Lys Gly His Asp Gly Leu Tyr Gln Gly
        515                 520                 525

Leu Ser Thr Ala Thr Lys Asp Thr Tyr Asp Ala Leu His Met Gln Ala
    530                 535                 540

Leu Pro Pro Arg
545

<210> SEQ ID NO 11
<211> LENGTH: 484
<212> TYPE: PRT
<213> ORGANISM: Artificial Sequence
<220> FEATURE:
<223> OTHER INFORMATION: Synthetic

<400> SEQUENCE: 11

Met Val Leu Leu Val Thr Ser Leu Leu Leu Cys Glu Leu Pro His Pro
1               5                   10                  15

Ala Phe Leu Leu Ile Pro Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Asn Leu Ala Trp Tyr Gln Gln Lys Pro Gly Lys
    50                  55                  60

Ala Pro Lys Arg Leu Ile Tyr Ala Ala Ser Asn Leu Gln Ser Gly Val
65                  70                  75                  80

Pro Ser Arg Phe Thr Gly Ser Gly Ser Gly Thr Glu Phe Thr Leu Ile
                85                  90                  95

Val Ser Ser Leu Gln Pro Glu Asp Phe Ala Thr Tyr Tyr Cys Leu Gln
            100                 105                 110

His His Ser Tyr Pro Leu Thr Ser Gly Gly Gly Thr Lys Val Glu Ile
        115                 120                 125

Lys Arg Thr Gly Ser Thr Ser Gly Ser Gly Lys Pro Gly Ser Gly Glu
    130                 135                 140

Gly Ser Glu Val Gln Val Leu Glu Ser Gly Gly Gly Leu Val Gln Pro
145                 150                 155                 160

Gly Gly Ser Leu Arg Leu Ser Cys Ala Ala Ser Gly Phe Thr Phe Ser
                165                 170                 175

Ser Tyr Ala Met Ser Trp Val Arg Gln Ala Pro Gly Lys Gly Leu Glu
            180                 185                 190

Trp Val Ser Ala Ile Ser Gly Ser Gly Gly Ser Thr Asn Tyr Ala Asp
        195                 200                 205

Ser Val Lys Gly Arg Phe Thr Ile Ser Arg Asp Asn Ser Lys Asn Thr
    210                 215                 220

Leu Tyr Leu Gln Met Asn Ser Leu Arg Ala Glu Asp Thr Ala Val Tyr
225                 230                 235                 240

Tyr Cys Ala Gly Ser Ser Gly Trp Ser Glu Tyr Trp Gly Gln Gly Thr
                245                 250                 255

```
Leu Val Thr Val Ser Ser Ala Ala Ile Glu Val Met Tyr Pro Pro
            260             265             270

Pro Tyr Leu Asp Asn Glu Lys Ser Asn Gly Thr Ile Ile His Val Lys
        275             280             285

Gly Lys His Leu Cys Pro Ser Pro Leu Phe Pro Gly Pro Ser Lys Pro
    290             295             300

Phe Trp Val Leu Val Val Gly Gly Val Leu Ala Cys Tyr Ser Leu
305             310             315             320

Leu Val Thr Val Ala Phe Ile Ile Phe Trp Val Arg Ser Lys Arg Ser
                325             330             335

Arg Leu Leu His Ser Asp Tyr Met Asn Met Thr Pro Arg Arg Pro Gly
            340             345             350

Pro Thr Arg Lys His Tyr Gln Pro Tyr Ala Pro Pro Arg Asp Phe Ala
        355             360             365

Ala Tyr Arg Ser Arg Val Lys Phe Ser Arg Ser Ala Asp Ala Pro Ala
    370             375             380

Tyr Gln Gln Gly Gln Asn Gln Leu Tyr Asn Glu Leu Asn Leu Gly Arg
385             390             395             400

Arg Glu Glu Tyr Asp Val Leu Asp Lys Arg Arg Gly Arg Asp Pro Glu
            405             410             415

Met Gly Gly Lys Pro Arg Arg Lys Asn Pro Gln Glu Gly Leu Tyr Asn
        420             425             430

Glu Leu Gln Lys Asp Lys Met Ala Glu Ala Tyr Ser Glu Ile Gly Met
    435             440             445

Lys Gly Glu Arg Arg Arg Gly Lys Gly His Asp Gly Leu Tyr Gln Gly
450             455             460

Leu Ser Thr Ala Thr Lys Asp Thr Tyr Asp Ala Leu His Met Gln Ala
465             470             475             480

Leu Pro Pro Arg

<210> SEQ ID NO 12
<211> LENGTH: 786
<212> TYPE: DNA
<213> ORGANISM: Artificial Sequence
<220> FEATURE:
<223> OTHER INFORMATION: Synthetic

<400> SEQUENCE: 12
atggttctgc tggtcaccag cctgctgctg tgcgaactgc cccaccccgc ctttctgctg    60
atccccgaca tccagatgac ccagagccct agcagcctga gcgccagcgt gggcgacaga   120
gtgaccatca cctgtcgggc cagccagggc atcagaaaca acctggcctg gtatcagcag   180
aagcccggca aggcccccaa gagactgatc tacgctgcca gcaatctgca gagcggcgtg   240
cccagcagat tcaccggaag cggctccggc accgagttca ccctgatcgt gtccagcctg   300
cagcccgagg acttcgccac ctactactgc ctgcagcacc acagctaccc tctgaccagc   360
ggcggaggca ccaaggtgga gatcaagcgg accggcagca ccagcggcag cggcaagcct   420
ggcagcggcg agggaagcga ggtccaggtg ctggaatctg gcggcggact ggtgcagcct   480
ggcggcagcc tgagactgag ctgtgccgcc agcggcttca ccttcagcag ctacgccatg   540
tcttgggtcc ggcaggctcc tggaaagggc ctgaatgggg tgtccgccat cagcggctct   600
ggcggctcca ccaactacgc cgacagcgtg aaggccggt tcaccatcag ccgggacaac   660
agcaagaaca ccctgtatct gcagatgaac agcctgagag ccgaggacac cgccgtgtac   720
```

```
tactgtgccg gcagcagcgg gtggagcgag tactggggcc agggcacact ggtcacagtg    780
tctagc                                                              786
```

<210> SEQ ID NO 13
<211> LENGTH: 1647
<212> TYPE: DNA
<213> ORGANISM: Artificial Sequence
<220> FEATURE:
<223> OTHER INFORMATION: Synthetic

<400> SEQUENCE: 13

```
atggttctgc tggtcaccag cctgctgctg tgcgaactgc cccacccgc ctttctgctg     60 atccccgaca tccagatgac ccagagccct agcagcctga gcgccagcgt gggcgacaga    120
gtgaccatca cctgtcgggc cagccagggc atcagaaaca acctggcctg gtatcagcag    180
aagcccggca aggcccccaa gagactgatc tacgctgcca gcaatctgca gagcggcgtg    240
cccagcagat tcaccggaag cggctccggc accgagttca ccctgatcgt gtccagcctg    300
cagcccgagg acttcgccac ctactactgc ctgcagcacc acagctaccc tctgaccagc    360
ggcggaggca ccaaggtgga gatcaagcgg accggcagca ccagcggcag cggcaagcct    420
ggcagcggcg agggaagcga ggtccaggtg ctggaatctg gcggcggact ggtgcagcct    480
ggcggcagcc tgagactgag ctgtgccgcc agcggcttca ccttcagcag ctacgccatg    540
tcttgggtcc ggcaggctcc tggaaagggc ctggaatggg tgtccgccat cagcggctct    600
ggcggctcca ccaactacgc cgacagcgtg aagggccggt tcaccatcag ccgggacaac    660
agcaagaaca ccctgtatct gcagatgaac agcctgagag ccgaggacac cgccgtgtac    720
tactgtgccg gcagcagcgg gtggagcgag tactggggcc agggcacact ggtcacagtg    780
tctagcgcgg ccgcattcgt gccggtcttc ctgccagcga agcccaccac gacgccagcg    840
ccgcgaccac caacaccggc gcccaccatc gcgtcgcagc ccctgtccct gcgcccagag    900
gcgtgccggc cagcggcggg gggcgcagtg cacacgaggg ggctggactt cgcctgtgat    960
atctacatct gggcgccctt ggccgggact tgtgggtcc ttctcctgtc actggttatc    1020 acccttact gcaaccacag gaacaggagt aagaggagca ggctcctgca cagtgactac    1080
atgaacatga ctccccgccg ccccgggccc accgcaagc attaccagcc ctatgcccca    1140
ccacgcgact cgcagcccta tcgctcccgt ttctctgttg ttaaacgggg cagaaagaag    1200
ctcctgtata tattcaaaca accatttatg agaccagtac aaaactactc agaggaagat    1260
ggctgtagct gccgatttcc agaagaagaa gaaggaggat gtgaactgag agtgaagttc    1320
agcaggagcg cagacgcccc cgcgtaccag cagggccaga accagctcta taacgagctc    1380
aatctaggac gaagagagga gtacgatgtt ttggacaaga cgtggccg ggaccctgag    1440 atgggggaa agccgagaag gaagaaccct caggaaggcc tgtacaatga actgcagaaa    1500
gataagatgg cggaggccta cagtgagatt gggatgaaag cgagcgccg gaggggcaag    1560 gggcacgatg cctttacca gggtctcagt acagccacca aggacaccta cgacgccctt    1620
cacatgcagg ccctgccccc tcgctaa                                      1647
```

<210> SEQ ID NO 14
<211> LENGTH: 1455
<212> TYPE: DNA
<213> ORGANISM: Artificial Sequence
<220> FEATURE:
<223> OTHER INFORMATION: Synthetic -continued

<400> SEQUENCE: 14

```
atggttctgc tggtcaccag cctgctgctg tgcgaactgc cccacccgc ctttctgctg      60
atccccgaca tccagatgac ccagagccct agcagcctga gcgccagcgt gggcgacaga    120
gtgaccatca cctgtcgggc cagccagggc atcagaaaca acctggcctg tatcagcag    180
aagcccggca aggcccccaa gagactgatc tacgctgcca gcaatctgca gagcggcgtg    240
cccagcagat tcaccggaag cggctccggc accgagttca ccctgatcgt gtccagcctg    300
cagcccgagg acttcgccac ctactactgc ctgcagcacc acagctaccc tctgaccagc    360
ggcggaggca ccaaggtgga gatcaagcgg accggcagca ccagcggcag cggcaagcct    420
ggcagcggcg agggaagcga ggtccaggtg ctggaatctg gcggcggact ggtgcagcct    480
ggcggcagcc tgagactgag ctgtgccgcc agcggcttca ccttcagcag ctacgccatg    540
tcttgggtcc ggcaggctcc tggaaagggc ctggaatggg tgtccgccat cagcggctct    600
ggcggctcca ccaactacgc cgacagcgtg aagggccggt tcaccatcag ccggacaac    660
agcaagaaca ccctgtatct gcagatgaac agcctgagag ccgaggacac cgccgtgtac    720
tactgtgccg gcagcagcgg gtggagcgag tactggggcc agggcacact ggtcacagtg    780
tctagcgcgg ccgcaattga agttatgtat cctcctcctt acctagacaa tgagaagagc    840
aatggaacca ttatccatgt gaaagggaaa cacctttgtc caagtcccct atttcccgga    900
ccttctaagc ccttttgggt gctggtggtg gttggtggag tcctggcttg ctatagcttg    960
ctagtaacag tggcctttat tattttctgg gtgaggagta agaggagcag gctcctgcac   1020
agtgactaca tgaacatgac tccccgccgc cccgggccca cccgcaagca ttaccagccc   1080
tatgccccac cacgcgactt cgcagcctat cgctccagag tgaagttcag caggagcgca   1140
gacgccccg cgtaccagca gggccagaac cagctctata cgagctcaa tctaggacga   1200
agagaggagt acgatgtttt ggacaagaga cgtggccggg accctgagat ggggggaaag   1260
ccgagaagga agaaccctca ggaaggcctg tacaatgaac tgcagaaaga taagatggcg   1320
gaggcctaca gtgagattgg gatgaaaggc gagcgccgga ggggcaaggg gcacgatggc   1380
ctttaccagg gtctcagtac agccaccaag gacacctacg acgcccttca catgcaggcc   1440
ctgccccctc gctaa                                                    1455
```

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Arg Ala Ser Gln Gly Ile Arg Asn Asn Leu Ala
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Ala Ala Ser Asn Leu Gln Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Leu Gln His His Ser Tyr Pro Leu Thr
1               5

<210> SEQ ID NO 18
<211> LENGTH: 5
<212> TYPE: PRT
<213> ORGANISM: Artificial Sequence
<220> FEATURE:
<223> OTHER INFORMATION: Synthetic

<400> SEQUENCE: 18

Ser Tyr Ala Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Ala Ile Ser Gly Ser Gly Gly Ser Thr Asn Tyr Ala Asp Ser Val Lys
1               5                   10                  15

Gly

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Ser Ser Gly Trp Ser Glu Tyr
1               5

<210> SEQ ID NO 21
<211> LENGTH: 23
<212> TYPE: PRT
<213> ORGANISM: Artificial Sequence
<220> FEATURE:
<223> OTHER INFORMATION: Synthetic

<400> SEQUENCE: 21

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 22
<211> LENGTH: 15
<212> TYPE: PRT
<213> ORGANISM: Artificial Sequence
<220> FEATURE:
<223> OTHER INFORMATION: Synthetic

```
<400> SEQUENCE: 22

Trp Tyr Gln Gln Lys Pro Gly Lys Ala Pro Lys Arg Leu Ile Tyr
1               5                   10                  15

<210> SEQ ID NO 23
<211> LENGTH: 32
<212> TYPE: PRT
<213> ORGANISM: Artificial Sequence
<220> FEATURE:
<223> OTHER INFORMATION: Synthetic

<400> SEQUENCE: 23

Gly Val Pro Ser Arg Phe Thr Gly Ser Gly Ser Gly Thr Glu Phe Thr
1               5                   10                  15

Leu Ile Val Ser Ser Leu Gln Pro Glu Asp Phe Ala Thr Tyr Tyr Cys
            20                  25                  30

<210> SEQ ID NO 24
<211> LENGTH: 10
<212> TYPE: PRT
<213> ORGANISM: Artificial Sequence
<220> FEATURE:
<223> OTHER INFORMATION: Synthetic

<400> SEQUENCE: 24

Ser Gly Gly Gly Thr Lys Val Glu Ile Lys
1               5                   10

<210> SEQ ID NO 25
<211> LENGTH: 30
<212> TYPE: PRT
<213> ORGANISM: Artificial Sequence
<220> FEATURE:
<223> OTHER INFORMATION: Synthetic

<400> SEQUENCE: 25

Glu Val Gln Val Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Trp Val Arg Gln Ala Pro Gly Lys Gly Leu Glu Trp Val Ser
1               5                   10

<210> SEQ ID NO 27
<211> LENGTH: 32
<212> TYPE: PRT
<213> ORGANISM: Artificial Sequence
<220> FEATURE:
<223> OTHER INFORMATION: Synthetic

<400> SEQUENCE: 27

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Gly
            20                  25                  30
```

```
<210> SEQ ID NO 28
<211> LENGTH: 11
<212> TYPE: PRT
<213> ORGANISM: Artificial Sequence
<220> FEATURE:
<223> OTHER INFORMATION: Synthetic

<400> SEQUENCE: 28

Trp Gly Gln Gly Thr Leu Val Thr Val Ser Ser
1               5                   10
```